United States Patent
Liechty et al.

(10) Patent No.: US 11,833,172 B2
(45) Date of Patent: Dec. 5, 2023

(54) USE OF MICRORNA-146A AND NANOCERIA CONJUGATE TO IMPROVE WOUND HEALING AND PROMOTE TISSUE REGENERATION

(71) Applicants: THE REGENTS OF THE UNIVERSITY OF COLORADO, Denver, CO (US); UNIVERSITY OF CENTRAL FLORIDA RESEARCH FOUNDATION, INC., Orlando, FL (US); THE TRUSTEES OF THE UNIVERSITY OF PENNSYLVANIA, Philadelphia, PA (US)

(72) Inventors: Kenneth Liechty, Aurora, CO (US); Sudipta Seal, Orlando, FL (US); Robert Gorman, Philadelphia, PA (US)

(73) Assignees: THE REGENTS OF THE UNIVERSITY OF COLORADO, Denver, CO (US); UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 416 days.

(21) Appl. No.: 15/779,123

(22) PCT Filed: Nov. 23, 2016

(86) PCT No.: PCT/US2016/063540
§ 371 (c)(1),
(2) Date: May 25, 2018

(87) PCT Pub. No.: WO2017/091700
PCT Pub. Date: Jun. 1, 2017

(65) Prior Publication Data
US 2018/0344764 A1 Dec. 6, 2018

Related U.S. Application Data

(60) Provisional application No. 62/378,997, filed on Aug. 24, 2016, provisional application No. 62/259,909, filed on Nov. 25, 2015.

(51) Int. Cl.
| | | |
|---|---|---|
| *A61K 33/24* | (2019.01) | |
| *A61K 47/54* | (2017.01) | |
| *A61K 47/55* | (2017.01) | |
| *A61K 47/69* | (2017.01) | |
| *C12N 15/113* | (2010.01) | |
| *A61K 9/00* | (2006.01) | |
| *A61K 9/14* | (2006.01) | |
| *C01F 17/235* | (2020.01) | |
| *A61P 29/00* | (2006.01) | |
| *A61K 31/728* | (2006.01) | |
| *B82Y 5/00* | (2011.01) | |

(52) U.S. Cl.
CPC .......... *A61K 33/24* (2013.01); *A61K 9/0014* (2013.01); *A61K 9/0019* (2013.01); *A61K 9/14* (2013.01); *A61K 47/549* (2017.08); *A61K 47/55* (2017.08); *A61K 47/6923* (2017.08); *A61P 29/00* (2018.01); *C01F 17/235* (2020.01); *C12N 15/113* (2013.01); *A61K 31/728* (2013.01); *B82Y 5/00* (2013.01); *C12N 2310/141* (2013.01); *C12N 2310/351* (2013.01)

(58) Field of Classification Search
CPC .... A61K 31/728; A61K 33/24; A61K 47/549; A61K 47/55; A61K 47/6923; A61K 9/0014; A61K 9/0019; A61K 9/14; A61P 29/00; B82Y 5/00; C12N 15/113; C12N 2310/141; C12N 2310/351; C01F 17/0043; C01F 17/206
USPC ....................................... 424/93.21; 435/458
See application file for complete search history.

(56) References Cited

U.S. PATENT DOCUMENTS

| | | |
|---|---|---|
| 7,534,453 B1 | 5/2009 | Rzigalinski et al. |
| 2010/0098768 A1 | 4/2010 | Andreescu et al. |
| 2013/0195927 A1 | 8/2013 | Sudipta et al. |
| 2013/0273659 A1* | 10/2013 | Costanzo ............. A61K 31/713 435/455 |
| 2013/0330364 A1 | 12/2013 | Basu et al. |
| 2013/0337083 A1 | 12/2013 | Reed et al. |
| 2015/0232837 A1* | 8/2015 | Thibonnier ............. A61P 29/00 514/44 A |
| 2015/0045450 A1 | 12/2015 | Versaggi et al. |
| 2016/0022976 A1* | 1/2016 | Peyman ............. A61K 47/6929 600/407 |

FOREIGN PATENT DOCUMENTS

| | | | | |
|---|---|---|---|---|
| WO | WO-2005116226 A2 * | 12/2005 | ......... | A61K 51/1244 |
| WO | 2007002662 A2 | 1/2007 | | |
| WO | 2009132277 A1 | 10/2009 | | |
| WO | 2014013473 A1 | 1/2014 | | |

(Continued)

OTHER PUBLICATIONS

Bolley et al. Langmuir 2013, 29, 14639-14647. (Year: 2013).*
Kalashnikova, Irina et al., "Nanoceria Induce miR-146a Expression in Diabetic Wounds", Poster, 2014 MRS Fall Metting, Nov. 30-Dec. 5, 2014, Dec. 5, 2014, 1 page.
Alexander, Margaret et al., "Exosome-delivered microRNAs modulate the inflammatory response to endotoxin", Nature Communications; vol. 6, Jun. 18, 2015, 16 pages.
Celardo, Ivana et al., "Pharmacological potential of cerium oxide nanoparticles", Nanoscale; vol. 3 No. 4, 2011, pp. 1411-1420.
EPO, "Extended European Search Report", Application No. 16869250. 7, dated Jun. 27, 2019, 12 pages.

(Continued)

*Primary Examiner* — Janet L Epps-Smith
(74) *Attorney, Agent, or Firm* — Dorsey & Whitney, LLP

(57) ABSTRACT

The present disclosure relates to wound treatment and therapy and the promotion of tissue regeneration following injury. In particular, it relates to a microRNA-146a and nanoceria conjugate for improving wound healing and, in some embodiments, preventing adverse ventricular remodeling following myocardial infarction.

15 Claims, 28 Drawing Sheets

(56) References Cited

FOREIGN PATENT DOCUMENTS

| WO | 2014028493 A2 | 2/2014 | |
|---|---|---|---|
| WO | WO-2014147608 A1 * | 9/2014 | ......... A61K 31/7088 |
| WO | WO 2015/058037 | 4/2015 | |
| WO | WO-2015058037 A1 * | 4/2015 | ........... A61K 9/5192 |
| WO | WO-2016015027 A1 * | 1/2016 | ............ B82Y 15/00 |
| WO | WO 2016/141334 | 9/2016 | |

OTHER PUBLICATIONS

Kalashnikova, Irina et al., "Nanoceria-miRNA as a modulator of inflammation in diabetic wounds", Nanoscience Technology Center, Univ. of Florida, Apr. 15, 2015, 1 pages.

Kalashnikova, Irina et al., "Nanoceria-miRNA as a modulator of inflammation in diabetic wounds", Poster—Society for Biomaterials Annual Meeting, Apr. 15, 2015, 1 pages.

Xu, J. et al., "Cerium Oxide Nanoparticles Induce MIR-146A Expression in Diabetic Dermal Fibroblast", Wound Repair and Regeneration; vol. 22, No. 2, 2014, pp. A69.

Xu, Junwang et al., "Nanoceria-MicroRNA-146a Conjugate Improves Wound Healing by Reducing Reactive Oxygen Species and Regulating Macrophage Polarization", Scientific Poster Presentations: 2016 Clinical Congress; vol. 223, No. 4S2, Oct. 2016, pp. e157.

International Preliminary Report on Patentability for International (PCT) Patent Application No. PCT/US2016/063540, dated May 29, 2018, 11 pages.

Asati et al., "Surface-Charge-Dependent Cell Localization and Cytotoxicity of Cerium Oxide Nanoparticles," ACS Nano, vol. 4, No. 9. Sep. 2010, pp. 5321-5331.

Chigurupati et al., "Effects of cerium oxide nanoparticles on the growth of keratinocytes, fibroblasts and vascular endothelial cells in cutaneous wound healing," Biomaterials, vol. 34, No. 9, Mar. 2013, pp. 2194-2201.

Das et al., "Cerium oxide nanoparticles: applications and prospects in nanomedicine," Nanomedicine (London), vol. 8, No. 9, Sep. 2013, pp. 1483-1508.

Das et al., "The induction of angiogenesis by cerium oxide nanoparticles through the modulation of oxygen in intracellular environments," Biomaterials, vol. 33, No. 31, Nov. 2012, pp. 7746-7755.

Pan et al., "MS2 VLP-based delivery of microRNA-146a inhibits autoantibody production in lupus-prone mice," International Journal of Nanomedicine, vol. 7, 2012, pp. 5957-5967.

Singh et al., "Subcellular fate and off-target effects of siRNA, shRNA, and miRNA," Pharmaceutical Research, vol. 28, No. 12, Dec. 2011, pp. 2996-3015.

Wen et al., "A Novel Role of Matrix Metalloproteinase-8 in Macrophage Differentiation and Polarization," Journal of Biological Chemistry, vol. 290, No. 31, Jul. 2015, pp. 15158-19172.

International Search Report issued by the U.S. Patent and Trademark Office for International Patent Application No. PCT/US2016/063540, dated Jan. 11, 2017, 3 pages.

Written Opinion issued by the U.S. Patent and Trademark Office for International Patent Application No. PCT/US2016/063540, dated Jan. 11, 2017, 9 pages.

* cited by examiner

Non-Diabetic

Diabetic

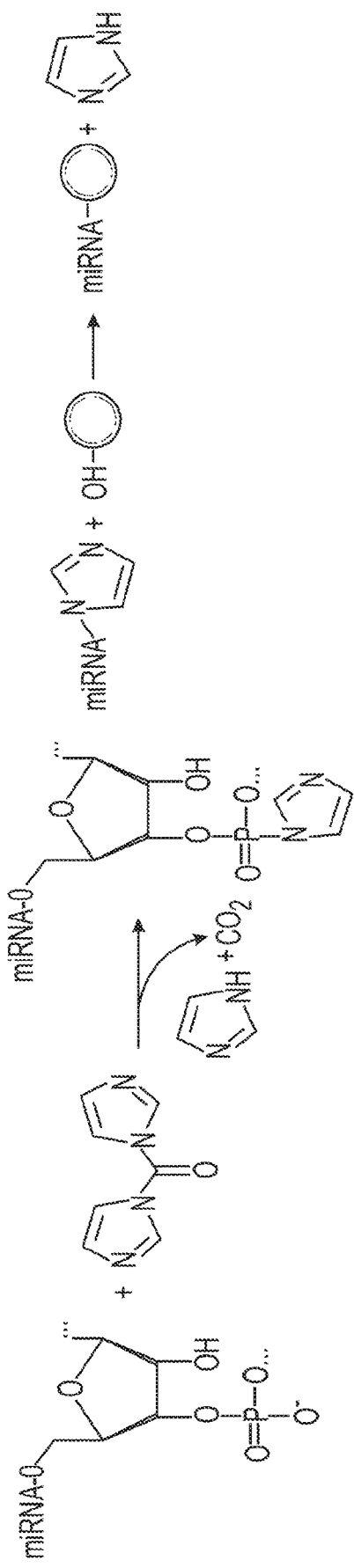
FIG. 17
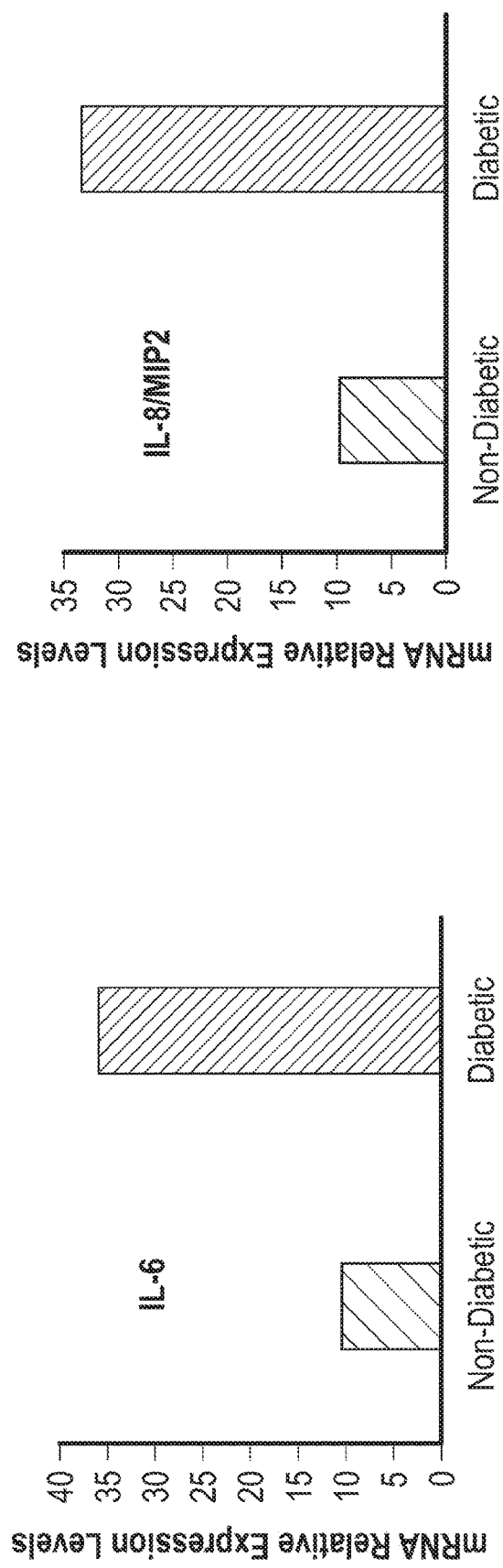
FIG. 18A
FIG. 18B

CNPs+miR146a or PBS
50 uL ID Injection of 10 uM Nanoceria
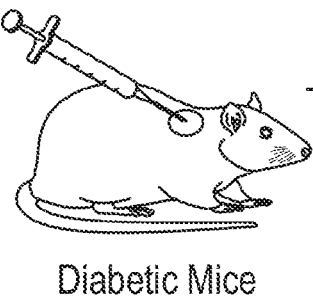
→ Day 3 and 10 →
Wound harvest
- Wound area
- MicroRNA expression
- Gene Expression
- Histology
Diabetic Mice
FIG. 28
Non-Diabetic
Day 0      Day 7      Day 10
 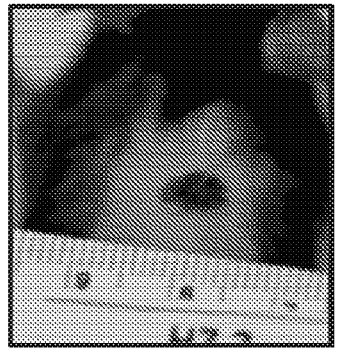 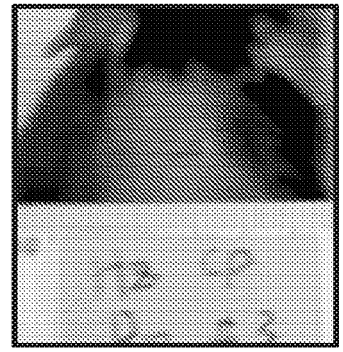
FIG. 29A
Diabetic
Day 0      Day 7      Day 10
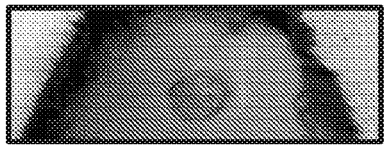 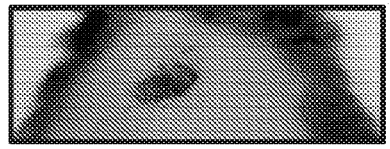 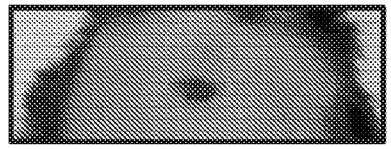
FIG. 29B

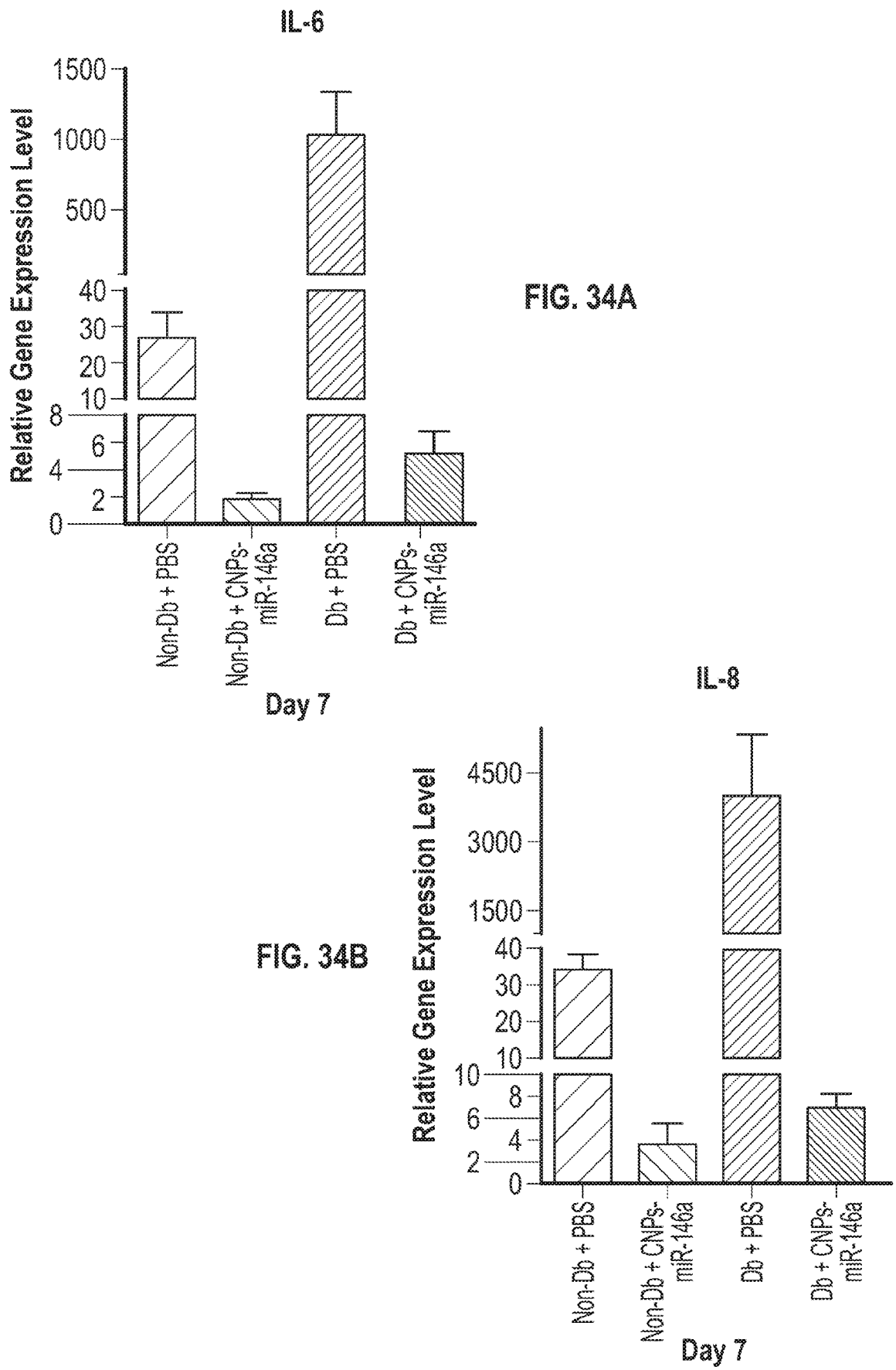

USE OF MICRORNA-146A AND NANOCERIA CONJUGATE TO IMPROVE WOUND HEALING AND PROMOTE TISSUE REGENERATION

CROSS REFERENCE TO RELATED APPLICATIONS

The present application is a national stage application under 35 U.S.C. 371 of PCT Application No. PCT/US2016/063540, having an international filing date of Nov. 23, 2016, which designated the United States, which PCT application claimed the benefit of U.S. provisional patent application U.S. Ser. No. 62/259,909, filed Nov. 25, 2015, and U.S. provisional patent application U.S. Ser. No. 62/378,997, filed Aug. 24, 2016, all of which are incorporated by reference herein in their entireties.

STATEMENT OF GOVERNMENT INTEREST

This invention was made with government support under grant numbers IDP2 DK083085-01 and R01-HL063964 both of which were awarded by the National Institutes of Health. The government has certain rights in the invention.

TECHNICAL FIELD

The present technology relates to wound treatment and therapy and the promotion of tissue regeneration following injury. More specifically, this technology relates to a microRNA-146a and cerium oxide nanoparticle (nanoceria) conjugate to improve wound healing and promote tissue regeneration.

BACKGROUND

Diabetes has reached pandemic proportions worldwide. Expenditures on diabetes care in the USA alone surpassed $174 billion in 2007. Complications of diabetes, such as impaired wound healing, represent a significant medical problem, with the annual cost of diabetic lower extremity ulcers alone exceeding 1.5 billion dollars. These chronic wounds result in significant morbidity for individuals including long hospitalizations, prolonged exposure to antibiotics, acute and chronic pain, the need for cumbersome wound care, and restricted mobility. In addition, an ulcer of the lower extremity precedes 84% of all diabetic lower extremity amputations, and is the primary cause for hospitalization among diabetics. Despite the enormous impact of these chronic wounds on both individuals and society, effective therapies are lacking. Thus, the modification, correction, or prevention of diabetes impaired wound healing has far-reaching consequences, both on patient outcomes and on healthcare expenditures.

Myocardial infarction (MI), commonly known as a heart attack, occurs when blood flow stops to a part of the heart resulting in damage to the heart muscle. On average, someone in the United States has a heart attack every 43 seconds. Damage to the heart muscle increases with time if blood flow to the affected tissue is not restored. In addition, adverse remodeling of the tissue in the affected area leads to further damage and loss of function in the ensuing weeks following the infarction. This adverse remodeling is responsible for 70% of heart failure and there is a 50% mortality within 5 years once heart failure occurs.

Normal wound repair and the response to injury follows an orderly and well-defined sequence of events that requires the interaction of many cell types, such as inflammatory cells, fibroblasts, keratinocytes, endothelial cells and progenitor cells, as well as the involvement of many growth factors, extracellular matrix (ECM) proteins, and enzymes. In diabetic wound healing, this complex orchestration of wound healing processes is disrupted and results in impaired healing. In the heart following MI, this process results in scar formation and a progressive decline in cardiac function.

SUMMARY

In one aspect, the present technology provides a method for treating or preventing inflammation in a subject in need thereof, the method comprising administering to the subject a therapeutically effective amount of a pharmaceutical composition comprising microRNA-conjugated cerium oxide nanoparticles (CNPs). In some embodiments, the inflammation is associated with a wound. In some embodiments, treating or preventing inflammation results in an increased rate of wound closure in the subject compared to the rate of wound closure in an untreated subject. In some embodiments, the subject is a diabetic subject.

In some embodiments of the methods of the present technology, the pharmaceutical composition is topically administered to the wound. In some embodiments, the pharmaceutical composition is administered a plurality of times. In some embodiments, the pharmaceutical composition is administered once. In some embodiments, the pharmaceutical composition is administered daily to the wound.

In some embodiments of the methods of the present technology, the subject is diagnosed as having a myocardial infarction. In some embodiments, the inflammation is associated with myocardial infarction. In some embodiments, the treatment or prevention comprises reducing left ventricular end-diastolic volume (LVEDV) in the subject relative to an untreated control. In some embodiments, the pharmaceutical composition is administered by injection to the site of the infarction.

In some embodiments, the pharmaceutical composition is administered to the subject about 1 hour, about 2 hours, about 3 hours, about 4 hours, about 6 hours, about 8 hours, about 12 hours, about 18 hours, about 24 hours, or about 48 hours following cardiac infarction. In some embodiments, the pharmaceutical composition is administered to the subject a plurality of times within the first week following cardiac infarction.

In some embodiments of the methods of the present technology, the treatment or prevention comprises reducing the expression level of one or more of IL-6, IL-8, TRAF6, IRAK1, and NFκB in the subject relative to an untreated control.

In some embodiments, the treatment or prevention comprises reducing the expression level of one or more of TNF-a, IL-6, CD64, IDO, SOCS1, and CXCL10 in macrophages in a subject in need thereof relative to an untreated control. In some embodiments, the treatment or prevention comprises increasing the expression level of one or more of MMP-8, MRC1, TGM2, CD23, and CCL22 in macrophages in a subject in need thereof relative to an untreated control. In some embodiments, the treatment or prevention comprises increasing the percentage of M2 macrophages relative to M1 macrophages in the subject's macrophage pool.

In some embodiments, administration of the microRNA-conjugated cerium oxide nanoparticles (CNPs) treats or prevents oxidative stress in the subject.

In another aspect, the present technology provides a method for treating or preventing oxidative stress in a subject in need thereof, the method comprising administering to the subject a therapeutically effective amount of a pharmaceutical composition comprising microRNA-conjugated cerium oxide nanoparticles (CNPs). In some embodiments, the oxidative stress is associated with a wound. In some embodiments, the treating or preventing oxidative stress results in an increased rate of wound closure in the subject compared to the rate of wound closure in an untreated subject. In some embodiments, the subject is a diabetic subject.

In some embodiments of the methods of the present technology, the pharmaceutical composition is topically administered to the wound. In some embodiments, the pharmaceutical composition is administered a plurality of times. In some embodiments, the pharmaceutical composition is administered once. In some embodiments, the pharmaceutical composition is administered daily to the wound.

In some embodiments, the subject is diagnosed as having a myocardial infarction. In some embodiments, the oxidative stress is associated with myocardial infarction. In some embodiments, the treatment or prevention comprises reducing left ventricular end diastolic volume (LVEDV) in the subject relative to an untreated control. In some embodiments, the pharmaceutical composition is administered by injection to the site of the infarction.

In some embodiments, the pharmaceutical composition is administered to the subject about 1 hour, about 2 hours, about 3 hours, about 4 hours, about 6 hours, about 8 hours, about 12 hours, about 18 hours, about 24 hours, or about 48 hours following cardiac infarction. In some embodiments, the pharmaceutical composition is administered to the subject a plurality of times within the first week following cardiac infarction.

In some embodiments of the methods of the present technology, the treatment or prevention comprises reducing the expression level of NOX2 in the subject relative to an untreated control.

In some embodiments of the methods of the present technology, the microRNA comprises miRNA-146a. In some embodiments, the surface of the CNPs is coated with one or more biocompatible molecules selected from hyaluronic acid, collagen, and fibrinogen. In some embodiments, the CNPs have a size range of about 3-5 nm. In some embodiments, the CNPs are doped with a lanthanide selected from one or more of Europium (Eu), Lanthanum (La), Praseodymium (Pr), Neodymium (Nd), Promethium (Pm), Samarium (Sm), Gadolinium (Gd), Terbium (Tb), Dysprosium (Dy), Homium (Ho), Erbium (Er), Thulium (Tm), Ytterbium (Yb), and Lutetium (Lu).

In some embodiments of the methods of the present technology, the administering is performed topically, intradermally, or intramuscularly.

In another aspect, the present technology provides a pharmaceutical composition comprising miRNA146a-conjugated cerium oxide nanoparticles (CNPs), wherein the miRNA146a-conjugated cerium oxide nanoparticles (CNPs) are configured to synergistically reduce oxidative stress and inflammation. In some embodiments, the surface of the CNPs is coated with one or more biocompatible molecules selected from hyaluronic acid, collagen, and fibrinogen. In some embodiments, the CNPs have a size range of about 3-5 nm. In some embodiments, the CNPs are doped with a lanthanide selected from one or more of Europium (Eu), Lanthanum (La), Praseodymium (Pr), Neodymium (Nd), Promethium (Pm), Samarium (Sm), Gadolinium (Gd), Terbium (Tb), Dysprosium (Dy), Homium (Ho), Erbium (Er), Thulium (Tm), Ytterbium (Yb), and Lutetium (Lu).

BRIEF DESCRIPTION OF THE DRAWINGS

For a fuller understanding of the present technology, reference should be made to the following detailed description, taken in connection with the accompanying drawings, in which:

FIG. 14 is a schematic presentation of the mechanism of the conjugated CNP-miRNA-146a.

FIG. 17 is a schematic drawing illustrating the reaction between phosphate groups of miRNA and hydroxyl groups of CNPs via activation with carbonyldiimidazole.

FIGS. 18A-18B are graphs illustrating increased IL-6 (FIG. 18A) and IL-8/MIP2 (FIG. 18B) gene expression in vitro in diabetic fibroblasts relative to non-diabetic fibroblasts.

FIG. 28 is an illustration depicting the experimental design of the studies employing cerium oxide nanoparticles.

FIGS. 29A-29B are photographs showing that CNPs+miR-146a treatment enhances wound closure in non-diabetic mice (FIG. 29A) and diabetic mice (FIG. 29B).

FIG. 30 is a graph illustrating the wound area over time for diabetic and non-diabetic subjects acting as controls or receiving CNPs-miR-146a. At day 7, the plots proceed as follows from top to bottom: Db+PBS; Non-Db+PBS; DB+CNPs-miR-146a; and nonDB+CNPs-miR-146a.

FIG. 31 is a graph illustrating the percentage of original wound area of non-diabetic and diabetic wounds over time. Wounds were treated at the time of injury with vehicle control, CNP alone, or CNP-miR146a. At day 7, the plots proceed as follows from top to bottom: Diabetic Control; Diabetic CNP; Non-diabetic Control; and Diabetic CNP-miR146a.

FIGS. 34A-34B are graphs illustrating relative gene expression levels for IL-6 and IL-8 in wounds from diabetic and non-diabetic mice with and without CNP-miR146a at 7 days.

FIGS. 35A-35B are images (FIG. 35A) and a graph (FIG. 35B) illustrating the decreased inflammatory cells in wounds from diabetic and non-diabetic mice with and without CNP-miR146a.

FIG. 39 is a histogram illustrating that the microRNA/nanoceria conjugate prevents adverse remodeling following myocardial infarction. MI=untreated myocardial infarction (angled black line shading in the bar); N=treatment with nanoceria alone (solid black shading in the bar); NC=treatment with nanoceria/microRNA conjugate (black with white dot shading in the bar). Following MI there is progressive increase in the end diastolic volume of the ventricle consistent with the development of cardiomyopathy and development of heart failure. This dilation is partially decreased with CNP but not to baseline. Treatment with the CNP conjugate prevents ventricular remodeling and returns the volume to baseline. This demonstrates the synergistic effects of CNP and the conjugation of miR-146a.

FIGS. 40A-40B: CD45 immunohistochemistry demonstrates increased inflammatory cells in adult infarcts (FIG. 40B) compared to fetal infarcts (FIG. 40A) at 30 days. FIGS. 40C-40D: activated caspase-3 staining demonstrates persistent apoptosis in adult infarcts (FIG. 40D) compared to fetal infarct (FIG. 40C) at 30 days.

FIG. 42 is a histogram showing miR146a gene expression by adult cardiac fibroblasts treated with CNP-146a.

FIG. 43 is a histogram showing IL-6 gene expression by adult cardiac fibroblasts following treatment with CNP-miR146a.

DETAILED DESCRIPTION

Definitions

Figure 1:
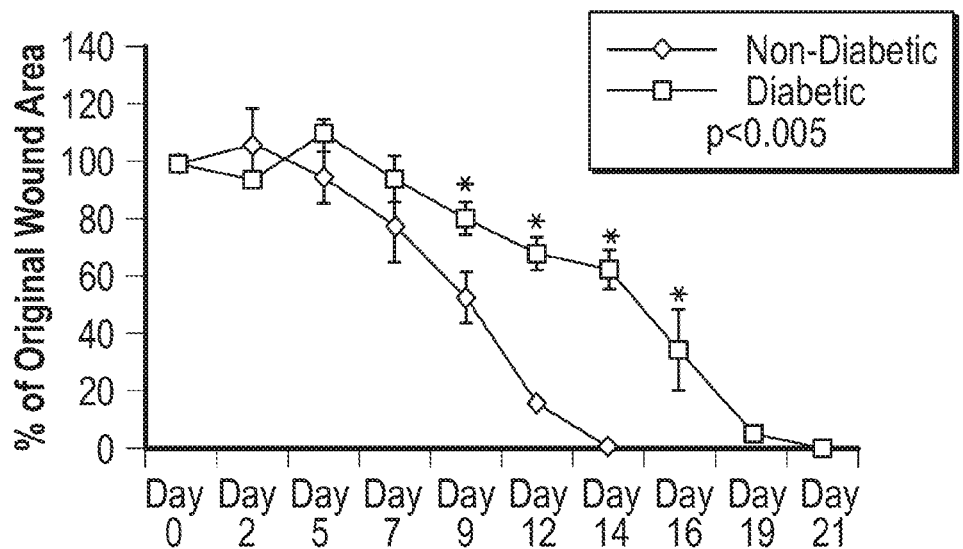
FIG. 1 is graph illustrating delayed wound healing in diabetic mice after injury.
Figure 2A:
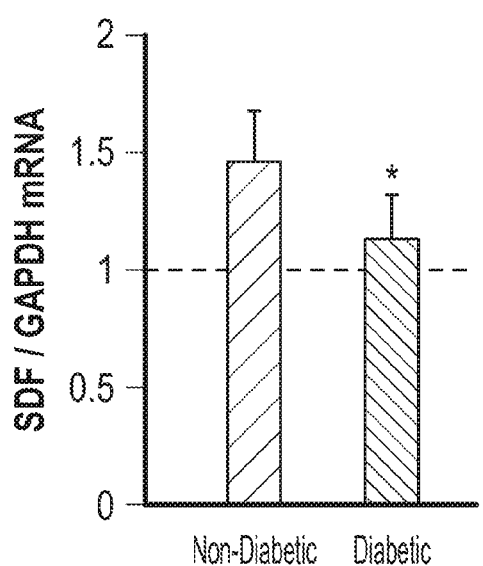
FIGS. 2A-2B are graphs illustrating decreased gene expression and protein production of SDF-1alpha in diabetic wounds.
Figure 2B:
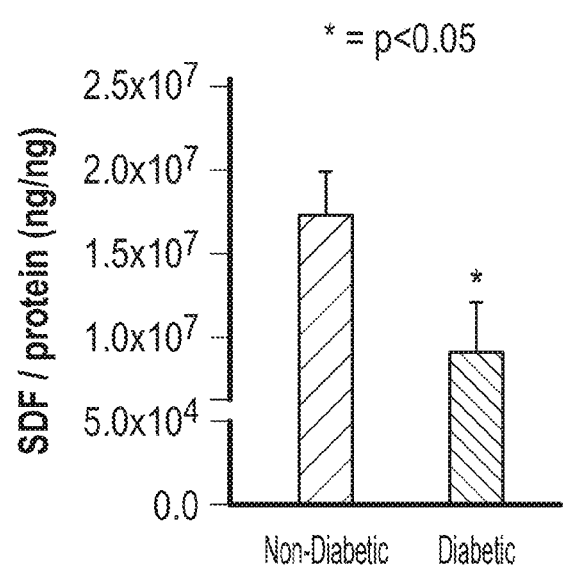

The definitions of certain terms as used in this specification are provided below. Unless defined otherwise, all technical and scientific terms used herein generally have the same meaning as commonly understood by one of ordinary skill in the art to which this present technology belongs.

The term "administration" and variants thereof (e.g., "administering" a compound) in reference to a compound of the present technology means introducing, by any route of introducing or delivering, the compound into the system of the subject in need of treatment. Any method of administration known to those in the art for contacting a cell, organ, or tissue with compositions, such as microRNA-CNP conjugates, may be employed. Suitable methods include in vitro, ex vivo, or in vivo methods. An effective amount of microRNA-CNP conjugates of the present technology useful in the present methods, such as in a pharmaceutical composition or medicament, may be administered to a subject in need thereof by any of a number of well-known methods for administering pharmaceutical compositions or medicaments. For example, the microRNA-CNP conjugates of the present technology may be administered systemically or locally. In some embodiments, the microRNA-CNP conjugates of the present technology may be administered orally, topically, intranasally, intramuscularly, subcutaneously, intradermally, intrathecally, intraperitoneally, or transdermally. In one embodiment, transdermal administration is by iontophoresis, in which the charged composition is delivered across the skin by an electric current. The schedule of doses is optimized to maintain the therapeutic concentration at the target tissue, such as by single daily or weekly administration, but also including multiple daily administrations, immediate treatment or delayed (e.g., 1-3 days after injury) with 0.1, 1, or 10 μg CNP conjugate.

As used herein, "cerium oxide nanoparticles," "$CeO_2$ nanoparticles," "nanoceria," or "CNPs" refer to cerium oxide nanoparticles, the synthesis of which has been described elsewhere. See, e.g., Chigurupati, et al., *Biomaterials* 34(9):2194-2201 (2013); U.S. Pat No. 7,534,453. In some embodiments, the CNPs have a size range of about 2-10 nm. In some embodiments, the CNPs have a size range of about 3-5 nm.

As used herein, the term "composition" is intended to encompass a product comprising the specified ingredients in the specified amounts, as well as any product which results, directly or indirectly, from combination of the specified ingredients in the specified amounts.

The term "diabetes," as used herein, includes both insulin-dependent diabetes mellitus (also known as type 1 diabetes) and non-insulin-dependent diabetes mellitus (also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Diabetes is characterized by a fasting plasma glucose level of greater than or equal to 126 mg/dL. A diabetic subject has a fasting plasma glucose level of greater than or equal to 126 mg/dL.

As used herein, "expression" denotes the product of an RNA produced through transcription of a gene or the production of the protein product encoded by a nucleotide sequence.

As used herein, "increased expression" or "increasing expression," indicate that expression of a particular gene sequence in a cell, tissue, organ, or organism has been increased relative to an untreated or control cell, tissue, organ, or organism.

"Increased rate of wound closure" as used herein refers to a decreased wound surface area and/or deceased percent (%) wound area in one subject relative to another over a period of time.

As used herein, "inflammation" is associated with or refers to inflammatory diseases or conditions including, but not limited to, wounds, scarring following injury in any organ or tissue, implants, arthritis, joint disease, vascular disease, aging, myocardial infarction, stroke, and traumatic brain injury.

A "pharmaceutically acceptable" component is one that is suitable for use with humans and/or animals without undue adverse side effects (such as toxicity, irritation, and allergic response) commensurate with a reasonable benefit/risk ratio.

A "pharmaceutical composition" refers to a composition that usually contains an excipient, such as a pharmaceutically acceptable carrier that is conventional in the art and that is suitable for administration to cells, organs, tissues, or a subject. In addition, compositions for topical and/or oral administration can be in the form of solutions, suspensions, tablets, pills, capsules, sustained-release formulations, oral rinses, or powders, as known in the art and described herein. The compositions also can include stabilizers and preservatives.

As used herein, "prevention" or "preventing" of a disorder or condition refers to one or more compounds that, in a statistical sample, reduces the occurrence of the disorder or condition in the treated sample relative to an untreated control sample, or delays the onset of one or more symptoms of the disorder or condition relative to the untreated control sample.

As used herein, "reduced expression," "reducing expression," or "suppressing expression," indicate that expression of a particular gene sequence in a cell, tissue, organ, or organism, has been decreased relative to an untreated or control cell, tissue, organ, or organism.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this technology.

As used herein, the terms "subject," "individual," or "patient" can be an individual organism, a vertebrate, a mammal, or a human.

As used herein, "synergy" or "synergistic effect" refers to a greater-than-additive effect, which is produced by a combination of at least two agents (e.g., nanoceria and microRNA), and which exceeds that which would otherwise result from the individual administration of the agents. For example, lower doses of one or more agents may be used in treating a disease or disorder, resulting in increased therapeutic efficacy and decreased side-effects.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. A therapeutically effective amount can be given in one or more administrations. The amount of a compound which constitutes a therapeutically effective amount will vary depending on the compound, the disorder and its severity, and the general health, age, sex, body weight and tolerance to drugs of the subject to be treated, but can be determined routinely by one of ordinary skill in the art.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder.

As used herein, "wound" refers to an injury to any tissue, including but not limited to, acute, subacute, delayed or difficult to heal wounds, and chronic wounds. Examples of wounds may include both open and closed wounds. Wounds may include, for example, diabetic wounds or ulcers, burns, incisions, excisions, lacerations, abrasions, puncture or penetrating wounds, surgical wounds, contusions, hematomas, crushing injuries, and ulcers.

A "delayed" or "difficult to heal" wound may include, for example, a wound that is characterized at least in part by one or more of: 1) a prolonged inflammatory phase, 2) a slow forming extracellular matrix (ECM), and 3) a stalled or decreased rate of epithelialization. As used herein, a "chronic wound" may refer to, for example, a wound that is characterized at least in part by one or more of: 1) a chronic self-perpetuating state of wound inflammation, 2) a deficient and defective wound ECM, 3) poorly responding (senescent) wound cells especially fibroblasts, limiting ECM production, and 4) failure of re-epithelialization due in part to lack of the necessary ECM orchestration and lack of scaffold for migration. Chronic wounds include diabetic wounds or ulcers, venous ulcers, arterial ulcers, pressure ulcers, and vasculitic ulcers.

In addition, "wounds" may also include, for example, injuries to the skin and subcutaneous tissue initiated by, for example, pressure sores from extended bed rest and wounds induced by trauma, and with varying characteristics. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I-III; examples of partial thickness wounds include pressure sores, venous stasis ulcers, and diabetic wounds or ulcers. The term "deep wound" is meant to include both Grade III and Grade IV wounds.

As used herein, "normal wound" refers to a wound as described above that is not a diabetic wound or ulcer.

The compositions and methods of the present technology provide for the treatment and prevention of all wound types, including normal wounds. In some embodiments, treating or preventing a wound encompasses reducing swelling, inflammation, and/or scar formation associated with the wound. In some embodiments, the compositions and methods of the present technology promote scarless wound healing. In some embodiments, the compositions and methods of the present technology accelerate the healing of normal wounds.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

Wound Healing and Ventricular Remodeling

Adverse remodeling is a significant clinical problem following myocardial infarction. In some embodiments, the present technology provides methods and compositions for treating or preventing ventricular remodeling following myocardial infarction (MI) in a subject in need thereof. In some embodiments, the present technology provides methods for treating or preventing ventricular remodeling following MI comprising administering a microRNA-nanoceria conjugate to a subject in need thereof. In some embodiments, the disclosure of the present technology relates to a microRNA-nanoceria conjugate that dramatically prevents ventricular remodeling following MI in a large animal model of myocardial infarction.

Impaired wound healing following injury in diabetic subjects represents a major clinical problem, resulting in prolonged hospitalizations and significant healthcare expenditures. Two-thirds of all non-traumatic amputations are preceded by a diabetic wound, and every 30 seconds, a lower limb is lost to a diabetic wound. The impaired healing of diabetic wounds is multifactorial and has been characterized by decreased production of chemokines, decreased angiogenesis, and an abnormal inflammatory response. Increasing evidence suggests that the persistent up-regulation of inflammatory gene expression may contribute to the pathogenesis of the chronic diabetic wound through activation of inflammatory pathways. One of the mechanisms of mesenchymal stem cell (MSC) correction of the diabetic wound healing impairment is through decreasing the inflammatory response.

Inflammation is an important component of normal wound healing. However, increased or persistent inflammation results in the accumulation of reactive oxygen species (ROS) and increased oxidative stress. In some embodiments, the present technology provides cerium oxide nanoparticle (CNPs) compositions. In some embodiments, the CNPs of the present technology may scavenge excess ROS, similar to the catalytic activity of superoxide dismutase (SOD) and catalase. In some embodiments of the present technology, the CNPs are useful in methods to accelerate the healing of wounds in a subject in need thereof compared to the rate of wound healing in an untreated subject. In some embodiments, the CNPs are useful in methods to accelerate healing of excisional wounds in a subject in need thereof compared to the rate of wound healing in an untreated subject.

The regulation of the inflammatory response occurs at multiple levels. MicroRNAs (miR or miRNA) are small noncoding RNA molecules involved in the posttranscriptional regulation of gene expression. In particular, miR-146a acts as the "molecular brake" on the inflammatory response, by targeting and repressing the activation of the NFκB inflammatory pathway. Expression of miR-146a is significantly down-regulated in diabetic wounds and MSC correction of the wound healing impairment is associated with increased miR-146a expression and down-regulation of inflammatory cytokine production. In some embodiments, the present technology provides compositions comprising miR-146a conjugated to the engineered CNPs described herein. In some embodiments, the present technology provides compositions and methods for the treatment of a wound in a subject in need thereof with miR-146a conjugated to the engineered CNPs described herein. In some embodiments, the present technology provides compositions and methods for the treatment of a diabetic wound in a subject in need thereof. In some embodiments, the present technology provides compositions and methods for the treatment of a diabetic wound in a subject in need thereof, wherein the compositions and methods can decrease the area of the diabetic wound, similar to the size of a non-diabetic wound at 7 and 10 days. In some embodiments, the present technology relates to engineering, optimizing, and synthesizing a formulation of engineered CNPs possessing properties that are able to overcome the increased inflammation and oxidative stress seen in diabetic wounds.

Chronic inflammation has been implicated as a major component in the pathogenesis of the diabetic wound healing impairment by increasing oxidative stress in the wound. It was observed that microRNA-146a and its targeted pro-inflammatory signaling pathways are dysregulated in diabetic subjects, resulting in increased and persistent inflammation (See, e.g., FIGS. 11, 12A, and 12B).

Dysregulation of miR-146a expression has been implicated in several chronic inflammatory diseases, as well as in the diabetic wound healing impairment. The expression of miR-146a is significantly down-regulated in diabetic wounds (FIG. 11) and that MSC correction of the wound healing impairment is associated with increased miR-146a expression and down-regulation of inflammatory cytokine production.

In some embodiments, the present technology provides compositions and methods for the treatment of wounds in a subject in need thereof with miR-146a conjugated to the CNPs described herein. In some embodiments, treatment of a diabetic wound with miR-146a conjugated to the CNPs of the present technology can decrease the area of the diabetic wound, similar to the size of a non-diabetic wound at 7 and 10 days. In some embodiments, the present technology relates to engineering, optimizing, and synthesizing a formulation of biocompatible coated CNPs possessing properties that are able to overcome the increased inflammation and oxidative stress seen in diabetic wounds and determining the mechanisms involved in this correction. In some embodiments, the present technology relates to the extension of these developments to show that these microRNA/nanoceria conjugates can be beneficially applied to the treatment of cardiac infarction.

Optimization of the combination of CNPs conjugated with miRNA-146a may decrease the inflammatory response, resulting in decreased ROS and oxidative stress and lead to improved diabetic wound healing. Similarly, optimization of the combination of CNPs conjugated with miRNA-146a may decrease the inflammatory response, resulting in decreased ROS and oxidative stress and lead to improved outcomes following cardiac infarction.

Figure 15A:
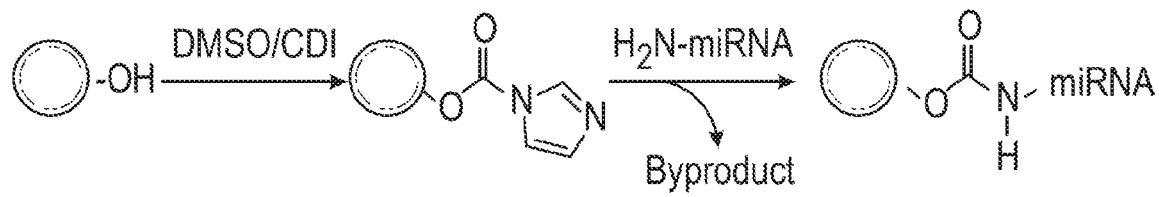
FIGS. 15A-15B are drawings illustrating the scheme of conjugating miRNA with bare CNPs using CDI chemistry (FIG. 15A) and the schematic presentation of three formulations of CNPs conjugated with miRNA (FIG. 15B): (1)-bare CNPs, (2)-CNPs coated with polysaccharide, (3)-X doped NPs (where X is a dopant such as a rare earth element from the lanthanide series).
Figures 1, 15B:
Figures 2, 15B:
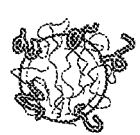
Figures 3, 15B:
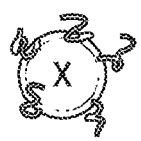

Diabetic mice have a significant delay in wound closure compared to non-diabetic mice (FIG. 1). This impairment is associated with significantly decreased production of granulation tissue and an increased epithelial gap, compared to non-diabetic wounds. The production of granulation tissue is dependent on the formation of new vessels in the wound bed, synthesis of extracellular matrix (ECM), and provides the substrate for epithelial cell migration and subsequent wound closure. Stromal derived factor-1α (SDF-1α or SDF-1alpha) is a potent chemokine that is involved in the early recruitment of progenitor cells, angiogenesis, formation of granulation tissue, and maintenance of the vascular system. SDF-1α actions are mediated through binding to the CXCR4 receptor and establishing a chemotactic gradient. The gene expression and protein production of SDF-1α in diabetic wounds 3 days following wounding has been examined. It was found that the diabetic wound healing impairment was associated with decreased SDF-1α gene expression and protein production in the wound 3 days following injury (FIG. 2).

Figure 3:
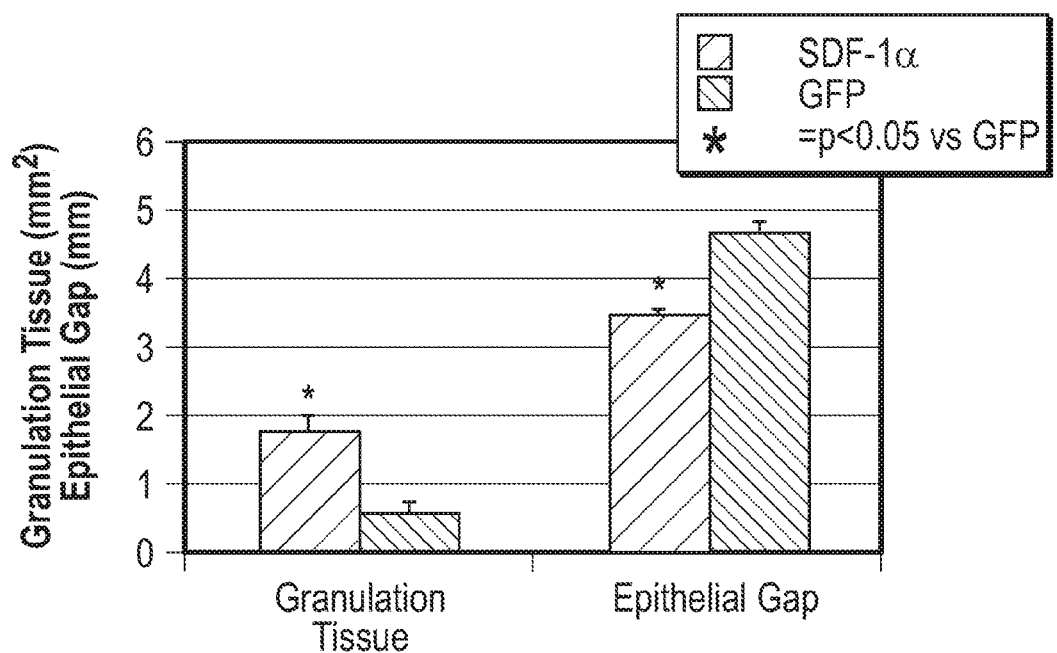
FIG. 3 is a graph illustrating the increased granulation tissue and epithelialization following treatment with lenti-SDF-1alpha.

Based on the findings that diabetic wounds have decreased SDF-1α levels relative to non-diabetic wounds, lentiviral-mediated overexpression of SDF-1α in diabetic wounds was examined to determine if that could correct the wound healing impairment. Disclosed herein is data demonstrating that lenti-SDF-1α treatment of diabetic wounds increased granulation tissue area and decreased the epithelial gap 7 days after treatment, compared to control lenti-GFP treated wounds (FIG. 3). These findings support targeting the SDF-1α receptor CXCR4 to correct the diabetic wound healing impairment.

In addition to impaired wound healing following injury, diabetics are predisposed to injury and the development of a chronic non-healing wound. Two-thirds of all non-traumatic amputations in the US are preceded by a diabetic foot wound. A significant factor that predisposes the diabetic to injury is the development of peripheral neuropathy, which affects up to 50% of patients with diabetes, resulting in altered perception of thermal, tactile, and vibrational stimuli. This has led to a focus on preventative measures to minimize foot damage in diabetic patients and decrease the incidence of non-healing diabetic wounds. However, many studies have demonstrated that physicians and patients are poorly compliant with simple foot care assessment programs.

Figure 4:
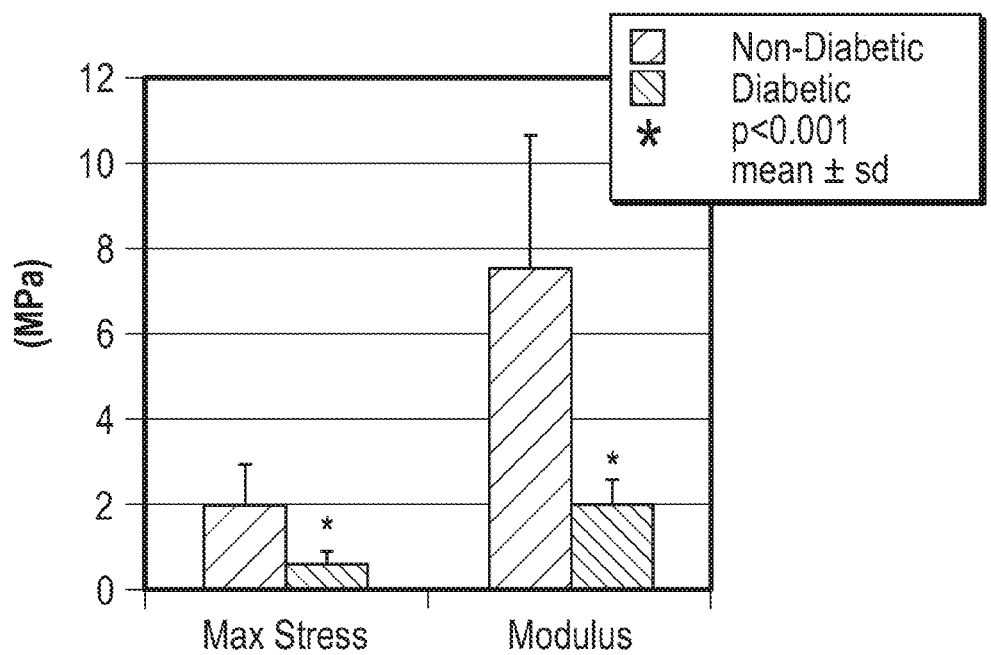
FIG. 4 is a graph illustrating the baseline impairment of ECM function in 12 week old murine diabetic skin.
Figure 5:
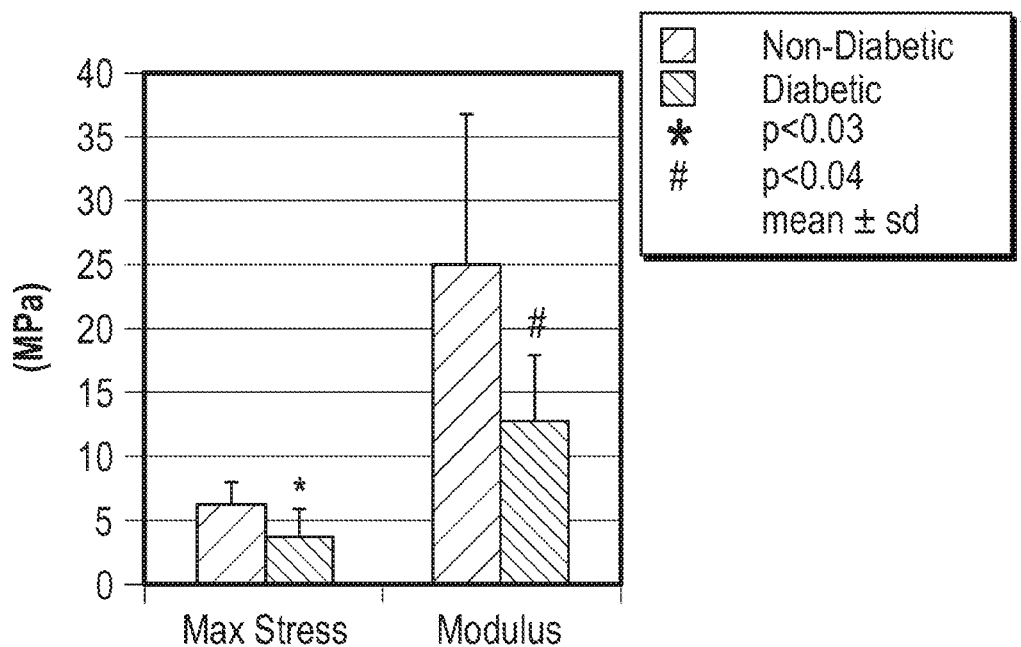
FIG. 5 is a graph illustrating the impaired ECM function in human diabetic skin.

Little research has focused on potential impairments in the diabetic skin at baseline that may predispose the diabetic skin to injury. Disclosed herein are the results of studies in which the biomechanical properties of diabetic skin in mice and humans at baseline were examined. Both murine (FIG. 4) and human (FIG. 5) diabetic skin demonstrated impaired skin integrity, with significantly inferior biomechanical properties at baseline. Both Max Stress and modulus were significantly decreased compared to non-diabetic skin, which may predispose the diabetic skin to injury.

Figure 6:
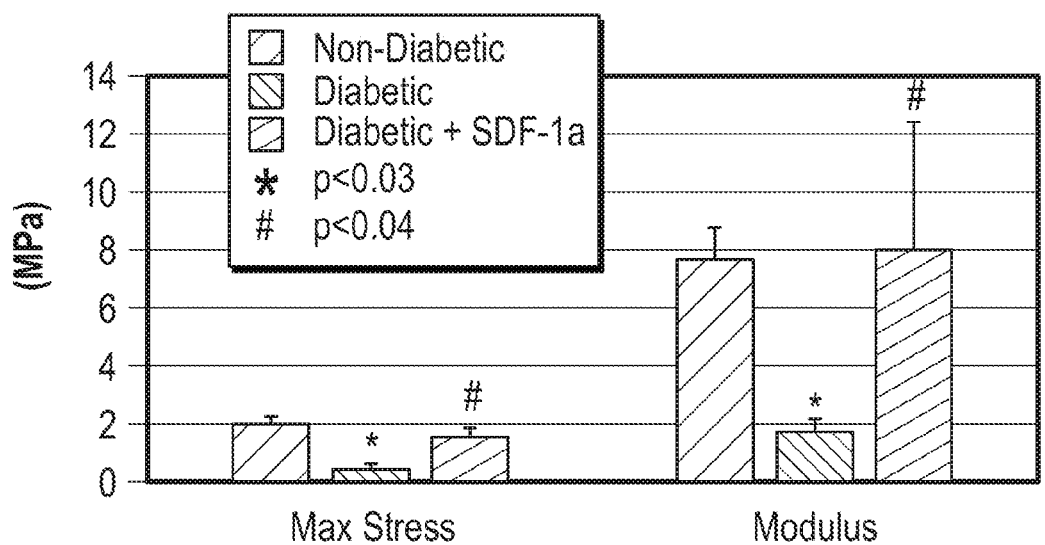
FIG. 6 is a graph illustrating improved biochemical properties of diabetic skin with SDF-1alpha treatment.

Based on the correction of the diabetic wound impairment with lenti-SDF-1α treatment, as shown above, the ability of lenti-SDF-1α treatment to correct the impaired biomechanical properties of diabetic skin at baseline was examined. The dorsal skin of 12-week old diabetic mice was injected with 108 pfu of lenti-SDF-1α and the site marked with India ink. The skin was then harvested after 28 days and the biomechanical properties assessed. As previously shown diabetic control skin had significantly impaired biomechanical properties compared to non-diabetic control skin (*=p<0.05). Lenti-SDF-1α treatment resulted in a significant improvement in diabetic skin integrity (#=p<0.01), with increased maximum stress and modulus to levels similar to the non-diabetic skin (FIG. 6).

This data demonstrates that deficient SDF-1α plays a central role in the diabetic wound healing impairment as well as the predisposition to injury. Correction of this deficiency improves diabetic wound healing and the impairment in the biomechanical properties of diabetic skin at baseline. This may decrease the susceptibility of diabetic skin to injury and aid in the prevention of the development of a chronic wound.

Figure 7A:
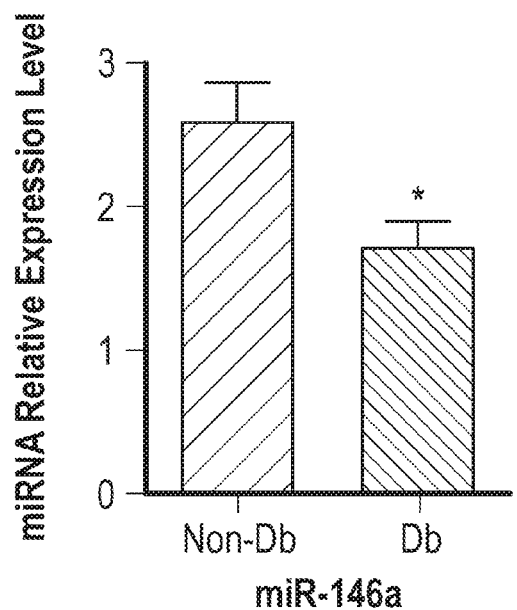
FIGS. 7A-7B are graphs illustrating the decreased miR-146a in human diabetic skin at baseline (FIG. 7A) and the correction of miR-146a production by diabetic fibroblasts with lentiviral SDF-1alpha (FIG. 7B).
Figure 7B:
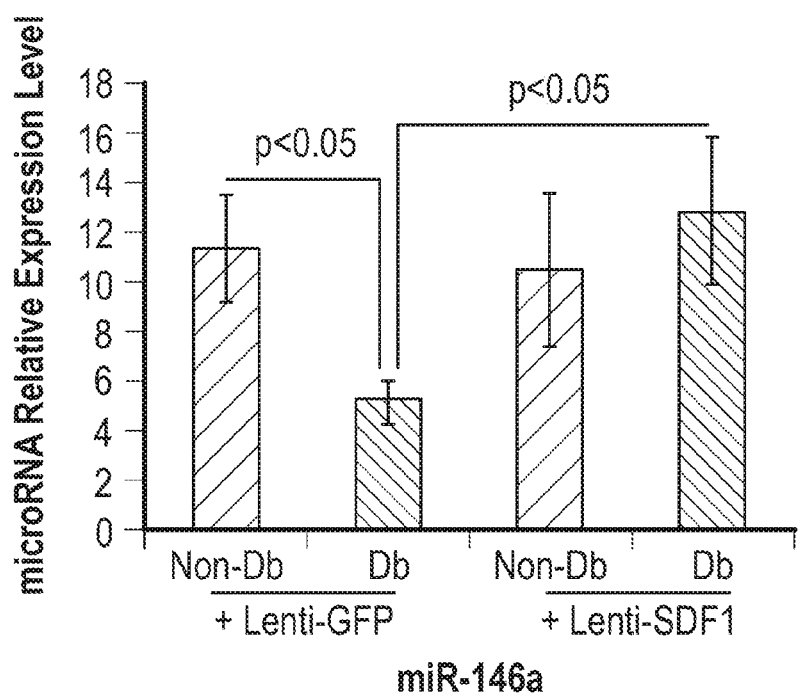
Figure 8:
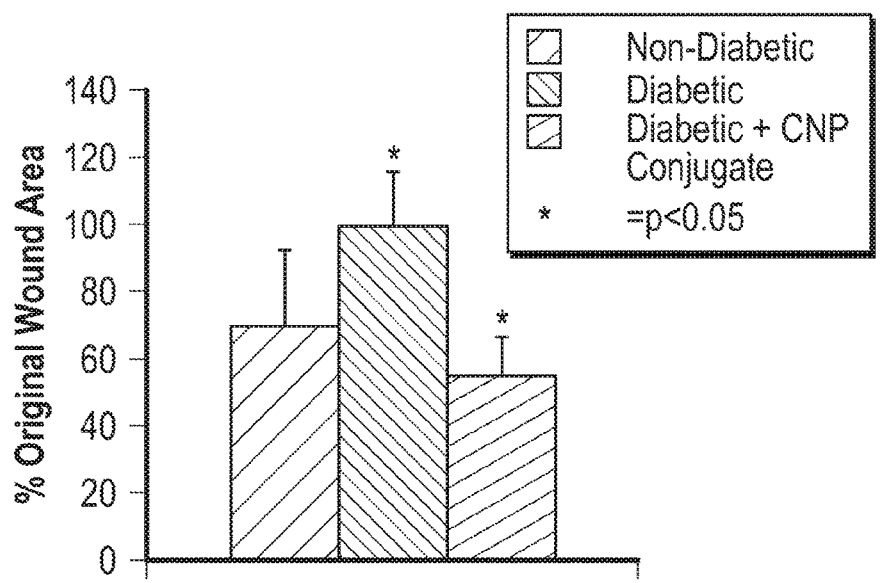
FIG. 8 is a graph illustrating the accelerated rate of wound healing in diabetic mice treated with CNP-miRNA conjugate. Shown is the % of original wound area at 7 days of 8 mm wounds in non-diabetic and diabetic mouse wounds. Treatment of the diabetic wounds with the CNP conjugate at the time of injury resulted in correction of the rate of closure to that of the non-diabetic.

Chronic inflammation is a key feature of diabetic wounds and has been implicated in the pathogenesis of this wound healing impairment. MicroRNA-146a (miR-146a) acts as a molecular brake on the inflammatory response by inhibiting signaling through NFκB, resulting in decreased production of the proinflammatory cytokines interleukin-6 (IL-6) and interleukin-8 (IL-8). Production of miR-146a is decreased in wounds and is associated with increased inflammation. Disclosed herein is data demonstrating that human skin at baseline has decreased miR-146a expression compared to non-diabetic skin (FIG. 7A). In vitro studies disclosed herein, show that diabetic fibroblasts also have decreased production of miR-146a compared to non-diabetic fibroblasts (FIG. 7B). As described above, data disclosed herein shows that SDF-1α can improve diabetic wound healing. Following on this, the effect of lentiviral mediated overexpression of SDF-1α on diabetic fibroblast expression of miR-146a was investigated. Data disclosed herein demonstrates that SDF-1α treatment increased expression of miR-146a in diabetic fibroblasts, similar to levels expressed by non-diabetic fibroblasts (FIG. 7B). Without wishing to be bound by theory, correction of miR-146a with SDF-1 α may explain, in part the wound healing correction and biomechanical property correction seen with SDF-1 α.

Macrophages are prominent in wounds where they exist in several different phenotypic states. Macrophages undergo specific differentiation depending on the local tissue environment, responding to environmental cues within tissues to differentiate into distinct functional phenotypes. M1 macrophages exhibit inflammatory functions. By contrast, M2 macrophages are characterized by their involvement in anti-inflammatory and tissue remodeling functions. M2 macrophages are further divided into M2a, M2b, M2c, and M2d phenotypes. Exemplary, non-limiting, phenotypic markers of M1 macrophages include TNF-a, IL-6, CD64, IDO (indoleamine), SOCS1 (suppressor of cytokine signaling 1), and CXCL10 (chemokine (C-X-X motif) ligand 10). Exemplary, non-limiting, phenotypic markers of M2 macrophages include MMP-8 (matrix metalloproteinase-8), MRC1 (mannose receptor C Type 1), TGM2 (transglutaminase 2), CD23, and CCL22 (chemokine (C-C motif) ligand 22). In some embodiments, the present technology provides compositions and methods for modulating macrophage polarization in a subject in need thereof by increasing M2 macrophage polarization or increasing the subject's M2 macrophage pool relative to an untreated control. In some embodiments, the present technology provides compositions and methods for modulating macrophage polarization in a subject in need thereof by increasing M2c macrophage polarization or increasing the subject's M2c macrophage pool relative to an untreated control. In some embodiments, the methods and compositions of the present technology increase the percentage of M2 macrophages relative to M1 macrophages in the subject's macrophage pool. The modulation or M2 polarization can be detected by measuring changes in the expression of M1 and M2 phenotype markers by methods known in the art.

EXAMPLES

Example 1

Figure 9A:
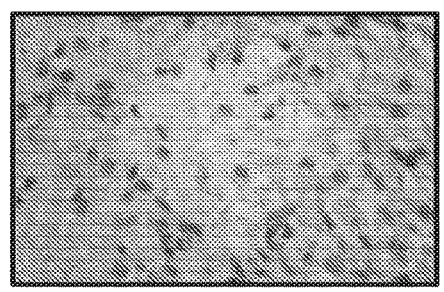
FIGS. 9A-9B are images illustrating increased CD45+ inflammatory cells in diabetic wounds (FIG. 9B) relative to non-diabetic wounds (FIG. 9A).
Figure 9B:
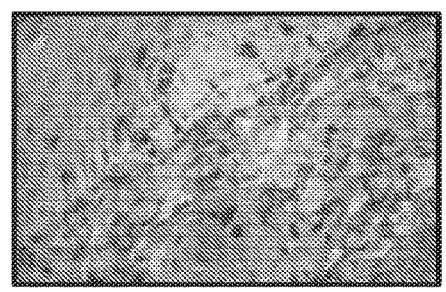

Engineering and Synthesis of MicroRNA-Conjugated and Biocompatible, Coated CNPs to Modulate the Inflammatory Response and Subsequent Oxidative Stress to Improve Diabetic Wound Healing Normal wound repair follows an orderly and well-defined sequence of events that requires the interaction of many cell types and growth factors, and is divided into the inflammatory, proliferative, and remodeling phases. In diabetic wound healing, this complex orchestration of wound healing processes and phases are disrupted. While the etiology is multifactorial, increased and persistent inflammation has been implicated as a central feature of the wound healing impairment in diabetics. Diabetic wounds have increased numbers of inflammatory cells at 7 days after wounding (FIGS. 9A-9B). The recruitment of inflammatory cells is, in part, regulated by proinflammatory cytokines, such as interleukin-6 (IL-6) and interleukin-8 (IL-8), which are produced by fibroblasts, endothelial cells, and macrophages in response to injury. These proinflammatory cytokines recruit inflammatory leukocytes, including polymorphonuclear cells, monocytes, and macrophages into the site of injury where they become activated and produce inflammatory cytokines, giving rise to additional inflammation and cytokine production. The increased inflammatory cells seen in diabetic wounds are associated with increased gene expression of the pro-inflammatory cytokines IL-6 (FIG. 10A) and MIP-2 (FIG. 10B), which is the murine equivalent of IL-8.

An additional layer of regulation of inflammation is at the level of protein synthesis. Recently, small RNA molecules or microRNA (miRNA) have been demonstrated to regulate the protein production of pro-inflammatory cytokines at the post-transcription level.

Figure 11:
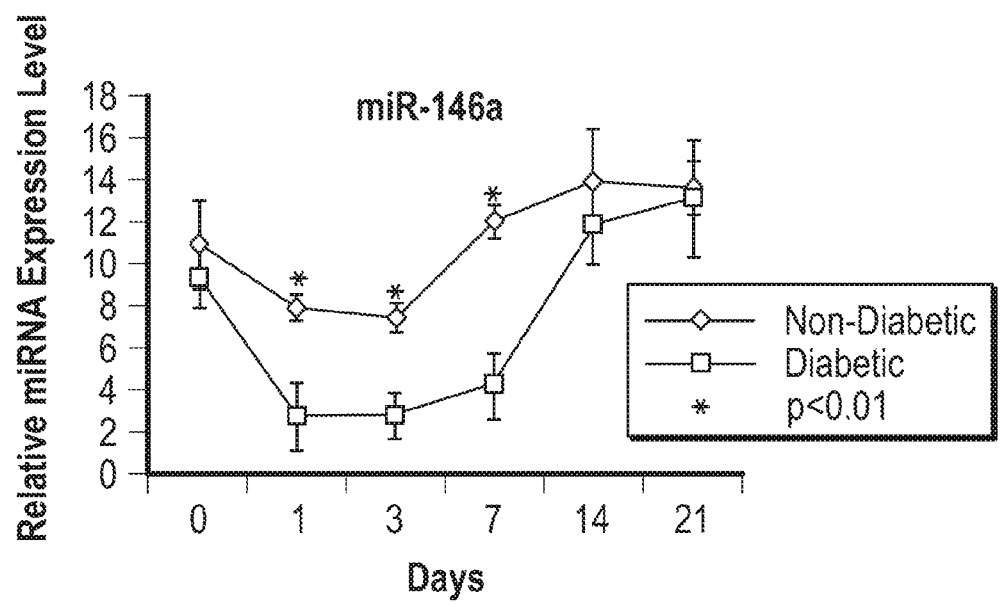
FIG. 11 is a graph illustrating decreased miR146a in diabetic wounds relative to non-diabetic wounds.

MiRNA bind to the 3' UTR of the target mRNA and results in mRNA degradation or translational repression. In particular, miR-146a has been described as one of the key regulatory molecules in the inflammatory response, acting as a "molecular brake" on the inflammatory response. MiRNA-146a suppresses the innate immune response by targeting and repressing interleukin-1 receptor associated kinase 1 (IRAK1) and tumor necrosis factor receptor associated factor 6 (TRAF6). These two key adapter molecules of the NF-κB pathway, increase NF-κB activity, resulting in increased expression of the genes IL-6 and IL-8. Diabetic wounds have decreased expression of miRNA-146a during the wound healing response (FIG. 11). Decreased miR-146a results in increased gene expression of its target genes, IRAK-1 (FIG. 12A) and TRAF-6 (FIG. 12B), as well as a subsequent increase in NF-κB signaling.

Without wishing to be bound by theory, decreased expression of miR-146a in diabetic wounds may be responsible for the increased gene expression of the proinflammatory cytokines IL-6 and IL-8/MIP-2 and the increased inflammation seen in diabetic wounds.

Nanoparticles have been used to deliver miRNA therapeutics to treat a number of different diseases and disorders. A recent publication has also shown that virus-like particles can act as carriers for miRNA-146a delivery and suppress the production of auto-antibodies in lupus-prone mice (Pan Y, Jia T, Zhang Y, Zhang K, Zhang R, Li J, et al., "MS2 VLP-based delivery of microRNA-146a inhibits autoantibody production in lupus-prone mice," *International Journal of Nanomedicine* 7:5957-5967 (2012)); however, the use of nanoparticles to deliver microRNA to correct the diabetic wound healing impairment or prevent adverse remodeling of the heart after myocardial infarction (MI) has not been investigated.

There are several barriers to miRNA delivery. MicroRNA travels inside of the cell through early endosomes, fusion to late endosomes, and then relocation to the lysosome. The acidic pH, which is lowered along this trafficking pathway, in addition to the sites for nuclease mediated miRNA degradation (Singh S, Narang A S, Mahato R I, "Subcellular fate and off-target effects of siRNA, shRNA, and miRNA," *Pharm. Res.* 28:2996-3015 (2011)), represent significant barriers to miRNA delivery. Nanovehicles can improve the therapeutic effect of miRNA by protecting it from degradation and mediating its entry into the cell. Cerium oxide nanoparticles (CNPs) traffic directly into the cytoplasm of a cell and escape the endosomal and lysosomal degradation pathway, providing for fast and safe delivery of miRNA.

Figure 13:
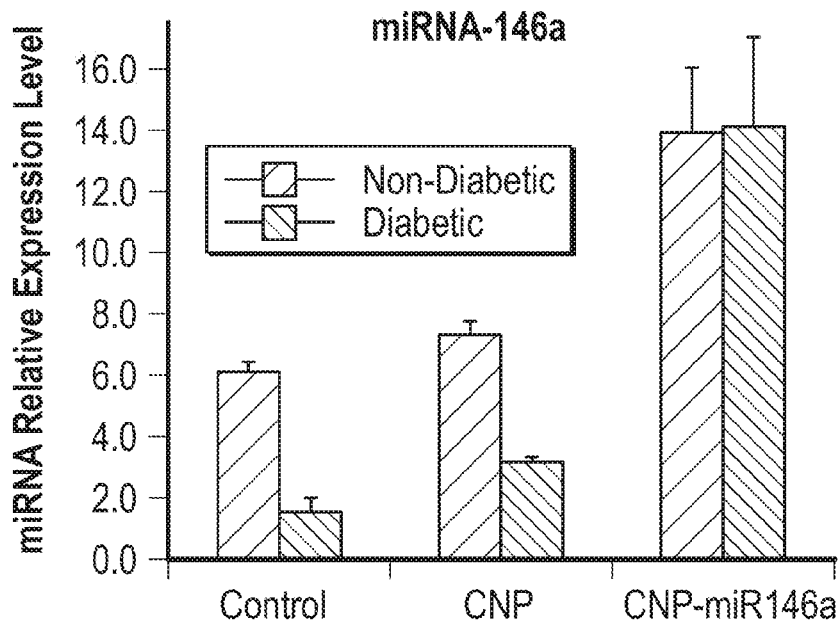
FIG. 13 is a graph illustrating the increased fibroblast expression of miR-146a with CNP-miR-146a conjugate treatment.

Disclosed herein are the results of studies aimed at examining the ability of a conjugate of miRNA-146a with engineered CNPs to deliver miRNA-146a to non-diabetic and diabetic fibroblasts. In some embodiments, treatment with the conjugate CNPs described herein resulted in correction of the diabetic fibroblast impairment in miRNA-146a expression with significant upregulation of miRNA-146a gene expression in both diabetic and non-diabetic fibroblasts (FIG. 13).

In addition to delivery of microRNA, CNPs have several advantages over current systems used in the miRNA delivery. CNPs are potent nano-inhibitors of oxidative stress due to their radical scavenging ability, similar to the enzymatic activity of superoxide dismutase (SOD) and catalase. (See, e.g., Das, et al., *Biomaterials* 33:7746-7755 (2012); Asati, et al., *ACS nano* 4:5321-5331 (2010); Chigurupati, et al., *Biomaterials* 34:2194-2201 (2013)). The dual role of targeting the inflammatory response with miR-146a delivery and decreasing oxidative stress via the CNPs radical-scavenging properties represents a novel and promising treatment to correct the diabetic wound healing impairment. In some embodiments, the engineered CNPs conjugated with miRNA-146a as described herein may correct the diabetic wound healing impairment by decreasing the inflammation response and oxidative stress seen in diabetic wounds.

CNP-miR-146a conjugates can improve diabetic wound healing impairment. The present technology provides a novel approach using CNPs to scavenge reactive oxygen species (ROS) and decrease oxidative stress. The use of miR-146a to target the inflammatory response in diabetic wounds is also a novel aspect of the present technology. In addition, in some embodiments, the present technology relates to the novel combination of CNPs and miR-146a to form a conjugate to produce synergistic effects on oxidative stress.

Figure 14:
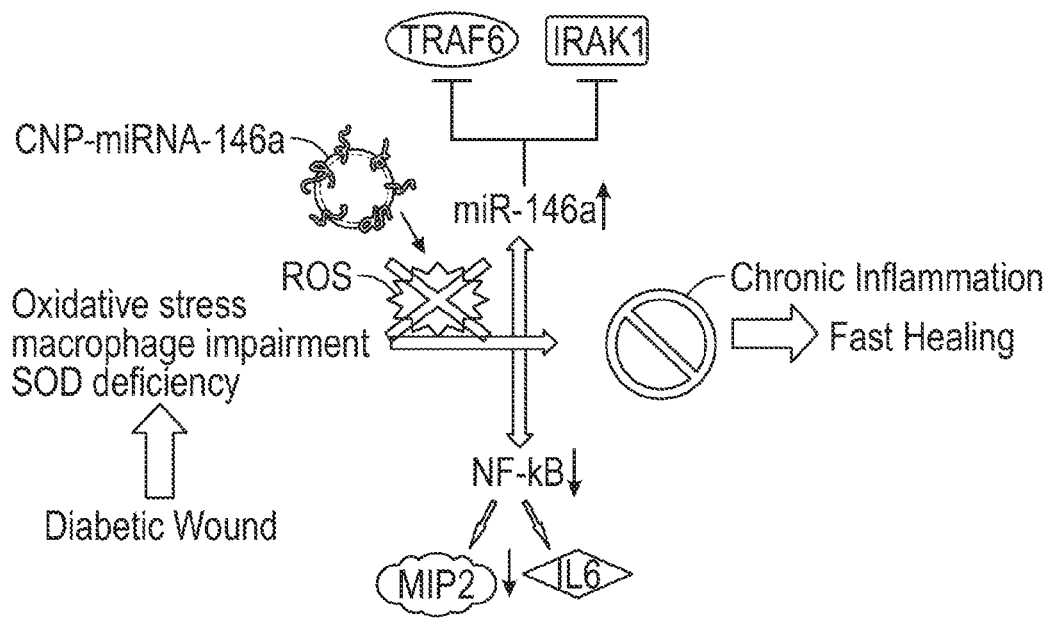

The present technology provides the engineering and synthesis of an absolutely novel formulation containing CNPs and miRNA-146a, possessing properties that are able to overcome impairments in diabetic wound healing. Without wishing to be bound by theory, one proposed mechanism of the conjugated CNPs application to the diabetic wounds is presented in the schematic in FIG. 14. The development of a better understanding of the fundamental properties of the conjugated CNPs, including: the preparation and formulation of the conjugated CNPs; their behavior inside a biological system; and the molecular and cellular responses in vitro and in vivo on the diabetic wound phenotype, as made possible in the present technology, provides a new type of delivery therapeutic for the diabetic wound healing impairment.

As previously discussed, diabetic patients have impaired wound healing that is multifactorial. However, a central feature of the diabetic wound is chronic inflammation and increased oxidative stress, which, as demonstrated herein, is associated with decreased levels of miR-146a. The radical-scavenging property of the CNPs described herein is facilitated by the ability of nanoceria to alternate its oxidation state between $3^+$ and $4^+$ oxidation states.

While the redox potential of CNPs favor the oxidation of cerium from $3^+$ to $4^+$ oxidation state to scavenge the ROS such as superoxide radical, the unique oxygen buffering capacity of nanoceria allows it to regenerate its trivalent oxidation state (for further scavenging of radicals) without entering into deleterious side reaction for regeneration. CNPs with high trivalent oxidation possess superoxide radical scavenging activity. CNPs of 3-5 nm size and with higher $Ce^{3+}/Ce^{4+}$ ratio are more active towards inducing angiogenesis and reducing the inflammation in both in vitro and in vivo model of normal wounds. Therefore, CNPs can be synthesized with higher $Ce^{3+}/Ce^{4+}$ ratio and doping can be used to increase the surface $Ce^{3+}$ ratio.

Nanoparticle bioavailability and tissue internalization can influence delivery of the microRNA. CNPs can be coated with biocompatible molecules to further enhance their utility. Bioavailability and internalization of CNPs can be enhanced by coating the nanoparticles with a biocompatible molecule. CNPs can be coated with hyaluronic acid, which has remarkable biological activities, including antibacterial, antimicrobial, anti-inflammatory, and wound healing accelerating properties. The wound-healing properties of hyaluronic acid are due to enhanced ECM remodeling, promotion of tissue granulation through fibroblast recruitment and enhancing keratinocyte proliferation and migration. Therefore, coating CNPs with hyaluronic acid may further strengthen the anti-inflammatory potential of CNPs and add new properties to the nanoparticles, such as increasing the ability to improve proliferation and remodeling phases of wound healing. Coating may change the extent of protein adsorption to the nanoparticle surface, improve their colloidal stability, and increase the number of functional groups for subsequent conjugation.

CNPs with a size range of 3-5 nm and a high $Ce^{3+}$ concentration enhanced angiogenesis and increased the rate of closure of full-thickness dermal wounds in a mouse model. See, e.g., Chigurupati, et al., *Biomaterials* 34(9):

2194-2201 (2013). In addition, the surface chemistry of nanoceria particles determines its antioxidant properties. Higher $Ce^{3+}$ on the surface increases the superoxide radical scavenging properties in biological environment. See, e.g., Das, et al., *Nanomedicine (Lond)* 8(9):1483-1503 (2013).

Therefore, increased $Ce^{3+}$ on the surface of the nanoparticles is proposed for better antioxidant properties. It is possible to increase the $Ce^{3+}$ by Eu doping. Described in further detail below is the successful conjugation of miRNA-146a for CNPs, and an in vitro cell culture study. Biocompatible coating on the surface of the nanoparticles can be used to improve the biocompatibility as well as catalytic activity. The same micro-RNA conjugation procedure can be used to conjugate microRNA on hyaluronic acid-coated nanoparticles. Conjugation of CNPs with microRNA had been performed in variable conditions, such as CNPs:microRNA ratio, reaction medium composition, temperature and pH, and during purification.

As the "seed region" in 5' end of the microRNA has to be perfectly complementary to the target mRNA for gene silencing, the attachment of miRNA-146a was performed via the amino group of the 3' end of the sequence. Disclosed herein is data demonstrating successful conjugation of CNPs with miRNA-146a (Table 1, FIG. 16D) with maintenance of biomolecule activity and colloidal stability of the suspension obtained. No precipitation or degradation of miRNA-146a on the top of CNPs was observed. As shown in FIG. 13, conjugated CNPs are more effective in up-regulating expression of miRNA-146a in both non-diabetic and diabetic fibroblasts compared to CNPs alone.

TABLE 1

Characterization of nanoparticle samples using UV-vis and DLS. Conjugates 1 and 2 were prepared using different ratio NPs:miR-146, 1:100 and 1:30, respectively; physical mixture of NPs with miRNA was made at ratio 1:100.

| Sample | miRNA content (ng/µl) | Zeta potential (mV) |
|---|---|---|
| CNPs | 0 | 37.2 |
| CNPs + miRNA | 11.3 | −29.1 |
| Conjugate 1 | 2.8 | −8.1 |
| Conjugate 2 | 25.2 | −18.0 |

Synthesis of lattice-substituted CNPs with altering $Ce^{3-}/Ce^{4-}$ and O vacancies: The ROS scavenging activity of CNPs are important for inflammation pathways during wound healing process. CNPs with a positive or neutral charge enter most cell lines and the CNP charge that determines activity is governed by the surface $Ce^{3+}/Ce^{4+}$ ratio. CNPs are redox-active owing to the coexistence of $Ce^{3+}/Ce^{4+}$ states and the compensating oxygen vacancies, which are more abundant at the surface. As a control, CNPs are be produced by simple chemistry. The CNP size is kept in the range of 3 to 5 nm with predominant $Ce^{3+}$ oxidation state. A trivalent element such as $La^{+3}$ (ionic radius 0.122 nm>$Ce^{+4}$ ionic radius 0.097 nm) is added in the $CeO_2$ crystal lattice, which leads to the formation of oxygen vacancies by replacing one $Ce^{4+}$ ion for every two trivalent ions in the $CeO_2$ lattice resulting in an increase in +3/+4 ratio and the oxygen vacancy concentration as follows:

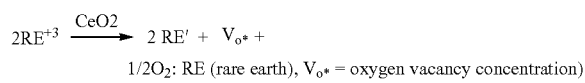

$1/2O_2$: RE (rare earth), $V_{o*}$ = oxygen vacancy concentration)

Doped and undoped CNPs with controlled size distribution can be synthesized by a microemulsion method. See, e.g., U.S. Pat. No. 7,534,453. Particles can be analyzed by ICP Mass Spectrometry for purity. The doped nanoceria sample is labeled as XCNP, where X is the dopant concentration (5, 10, 20 at % of La as rare earth dopants).

Surface coating of CNPs: Post-synthesis methods of surface coating can be performed by simple absorption of hyaluronic acid molecule on CNPs in a polysaccharide solution for 1 h. The layer of coating can be formed via hydrogen and dative bonds and electrostatic interactions. For covalent binding, carboxyl groups of hyarulonic acid can be activated with 1-ethyl-3 (dimethylaminopropyl) carbodiimide (EDC), which allows it to bond with the surface hydroxyl groups of the CNPs. Chemical attachment of the coating layer can be performed using bifunctional PEG spacer, for example poly (ethylene glycol) diglycidyl ether or heterobifuncational PEG spacer (epoxy-PEG-NHS, Silane-PEG-NHS) for the following conjugation with oligonucleotide.

Conjugation of CNPs with oligonucleotide: Oligonucleotides contain phosphate groups carrying a negative charge along the chain that can electrostatically interact with the positively charged surface of the CNPs. In addition, oligonucleotides have hydroxyl groups of ribose and amino groups available for conjugation with the CNPs. The terminal functional group (amino, thiol, azide) for conjugation is also an option. Following appropriate excess of oligonucleotide in reaction medium, basically 10-15 molecules per nanoparticle, conjugation can be accomplished via different reactions. For example, amino groups of oligonucleotide can be coupled with CNP hydroxyl groups or functional groups of CNP coating after their activation with carbodiimide (CDI) or other bifunctional activating agent (FIG. 15A). Conjugation of molecules with functional groups of coating has been demonstrated. Accordingly, microRNA attachment to the coating is contemplated by the present technology. Unbound compounds, as well as by-products, can be removed by centrifugation at 8000 g for 10 min and by dialysis against water or PBS using mini dialysis columns with at least 20 kDa cut off. FIG. 15B (1)-(3) shows the graphical representation of the three different formulations of CNPs.

Figure 16A:
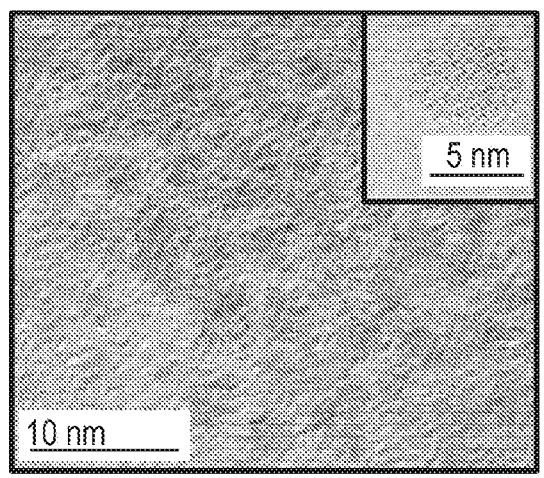
FIGS. 16A-16E show photographs (FIGS. 16A and 16B) and three graphs (FIGS. 16C-16E) illustrating (A) HR-TEM image of CNPs showing non-agglomerated nature (3-5 nm), (B) Selected area electron diffraction (SAED) pattern, (C) XPS spectra of +3/+4 states variation when 1 shows more +3 compared to 2, (D) FT-IR spectra of miRNA, physical mixture of miRNA and CNP, and conjugate CNPs with miRNA, (E) MTT test results of fibroblasts treatment with 10 uM of CNPs for 24 hrs.
Figure 16B:
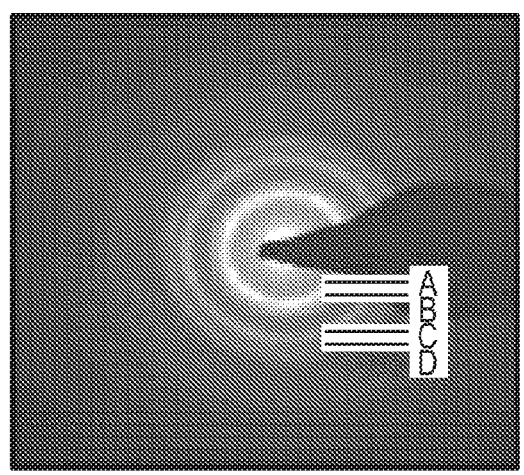
Figure 16C:
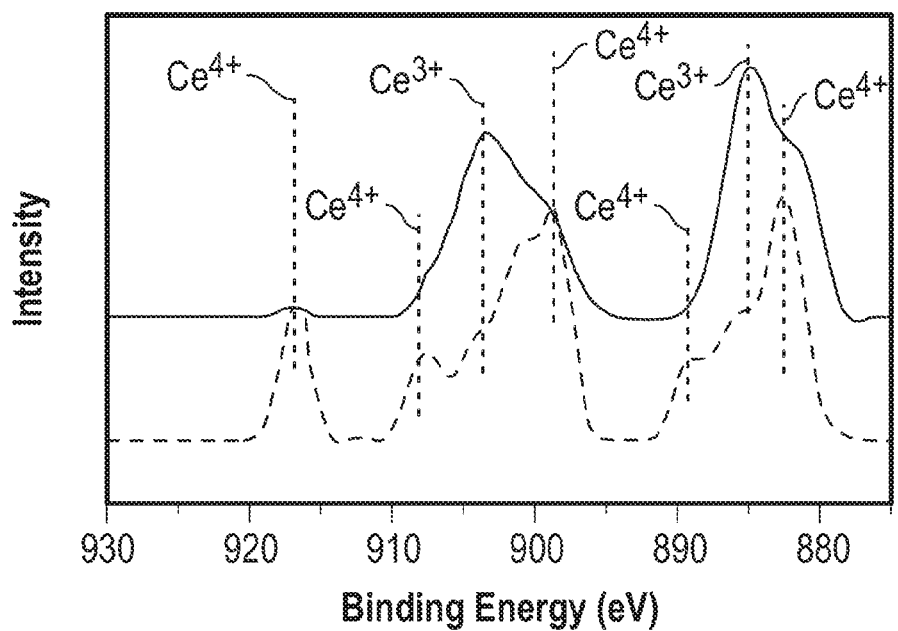

Detailed conjugated CNP characterization with Advanced Analytical Techniques: High Resolution Transmission Electron Microscopy (HRTEM) and Dynamic Light Scattering (DLS) can be used to determine the size and hydrodynamic radii of synthesized CNPs (Table 1, FIG. 16A). The selected area electron diffraction pattern confirms nanoceria are crystalline (FIG. 16B). Prepared samples can be characterized by DLS to confirm their colloidal stability. Electron Energy Loss Spectroscopy (EELS) can be carried out to study the +3/+4 ratio in the bulk of the particle. The Fourier transform infrared spectroscopy (FTIR) measurements can be done by PerkinElmer Spectrum One FT-IR spectrometer using the KBr pellet technique to determine the covalent bonds formed with CNPs surface during coating and conjugation (FIG. 16C). Characteristic bands at 3410, 1638, region 1340-1385, and 1250 $cm^{-1}$ are assigned to amide II and III. Formation of bonds with CNPs via phosphate can be indicated at 1088 and 1024 indicated at 1024 cm−1.

Figure 16D:
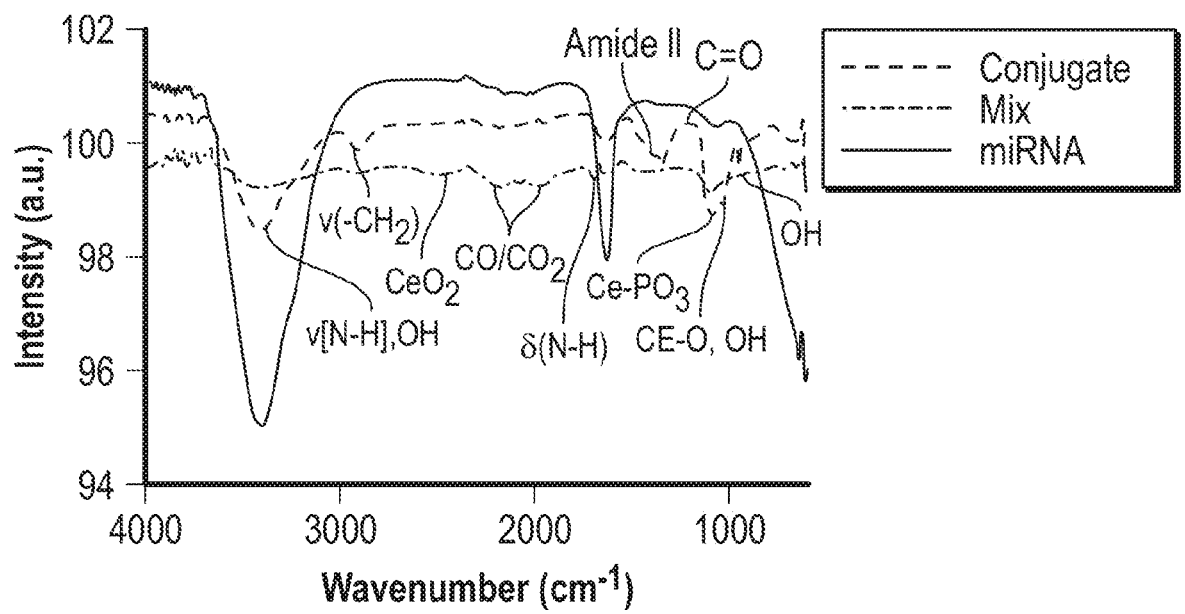
Figure 16E:
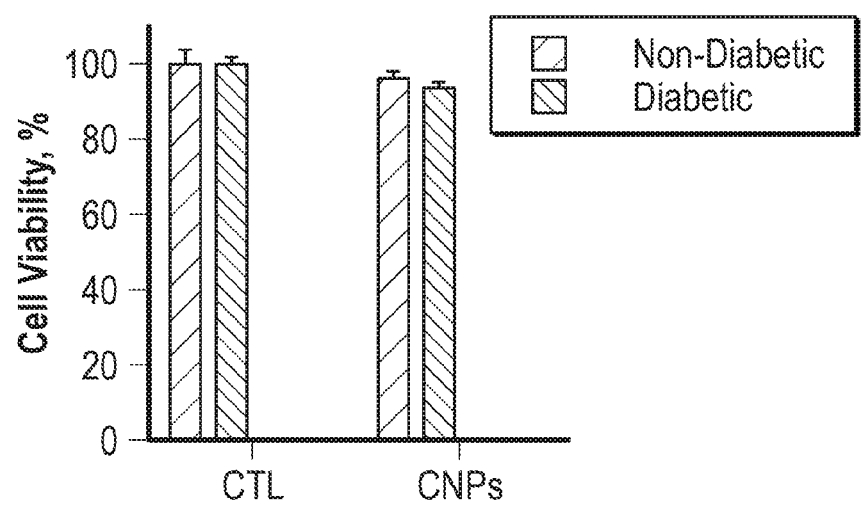

X-ray diffraction can be used for crystal structure characterization. X-ray Photoelectron Spectroscopy (XPS: 5400 Perkin Elmer, Mg anode, 200 W) high resolution scans can be used to determine the elemental composition and the mixed valence states of CeNPs (surface concentration of $Ce^{3+}/Ce^{4+}$) by deconvoluting the high resolution XPS $Ce^{3+}$ spectrum and is compared to O vacancy concentration (FIG. 16D). UV-Vis spectrophotometry is performed on PerkinElmer Lambda 750S UV-VIS spectrometer to collect the spectrum of bare CNPs and modified CNPs to confirm that coating and oligonucleotide are integral parts of the CNPs. This method can also be applied to analyze the amount of oligonucleotide conjugated with CNPs by NanoDrop® ND-1000 UV-Vis Spectrophotometer at 260 nm (Table 1). The number of miRNA molecules loaded on the nanoparticles can be estimated using thermogravimetric analysis. Engineered CNPs are nontoxic and have no adverse effect on cells or tissue using both in vitro and in vivo model systems. In order to examine toxicity of synthesized CNPs with or without conjugation, screening can be performed using cultured fibroblasts and keratinocytes using MTT testing and LDH analysis over a range of concentrations (0.01 µM to 100 µM). The MTT assay measures cell viability and proliferation (FIG. 16E). The yellow tetrazolium salt (MTT) can be reduced by metabolically active cells to generate a purple equivalents formazan dye that is quantified at 590 nm using a reference at 620 nm. Lactate dehydrogenase is indicator of cell membrane damage. LDH being released from the damaged cells can be measured at 340 nm in culture media using an enzymatic reaction resulting in a red formazan product formation.

In some embodiments, single CNPs can be synthesized with range size 3-5 nm based on TEM observation with predominant $Ce^{3+}$ oxidation state, as high as 60% by doping. Increased content of trivalent oxidation state of cerium will enlarge redox activity and thus the scavenging capacity of CNPs. In some embodiments, coating with hyaluronic acid may improve the biocompatibility and behavior of CNPs within wounds, changing its stability in the biofluids, preventing aggregation that causes cytotoxicity, changing the biodistribution profile due to acquired bioadhesive and biodegradable properties, as well as retention time within cellular space, mechanism of uptake and exocytosis. The coating may add some or all of the following abilities: antibacterial activity; accelerate infiltration of inflammatory cells; stimulate extracellular matrix deposition; induce fibroblast proliferation; enhance formation of granulation and early re-epithelialization; hemostatic efficiency with rapid blood clotting property; and increased wound contraction. MiR-146a delivery to the wound site or site of injury may correct the inflammatory response on the molecular level via suppressing pro-inflammatory genes expression and inflammation, decreasing oxidative stress, and preventing chronic wound formation. In some embodiments of the present technology, the conjugated CNPs shorten the time of diabetic wound closure and help avoid the complications associated with impaired diabetic wound healing.

Several strategies for chemical coupling and coating to the CNPs surface with microRNA can be used. Other agents, such PEG spacers can be used for the conjugation. Conjugation of CNPs with a targeting compound via PEG spacer improves the CNP biocompatibility. For instance, bifunctional poly(ethylene glycol)diglycidyl ether and heterobifuncational PEG spacer (epoxy-PEG-NHS, Silane-PEG-NHS), which can make a link between amino- and hydroxyl groups, or two amino groups. Varying terminal functional group at the end of microRNA may impact the chemistry strategy.

Side reactions might occur while microRNA are coupled to CNPs, since microRNA are rich in phosphate groups that can react with an excess of carbonylimidazole and then with the OH groups of the CNPs (FIG. 17). This reaction occurs depending on proton concentration and temperature. There are two features of the activated form of microRNA phosphate that may prevent this reaction. Monoimidazolyl phosphinate (FIG. 17(1)): it is conditionally stable in water above pH 7 and it will react with alcohols preferably rather than with amines. On one hand, this reaction will ensure the chemical attachment between microRNA and the nanoparticles. On the other hand, multi-coupling of microRNA to CNPs is possible that may alter the miRNA detachment and its interaction with targeting region of mRNA at the end.

Depending on CNP concentration, surface chemistry (charge), type of cells, and exposure time, cell viability is varied. Possible cytotoxicity of CNPs in vivo can be avoided via appropriate dosing based on the in vitro data of MTT and LDH assays.

Example 2

Determination of the Cellular Mechanisms and Optimization of the Modulation of the Inflammatory Response and Oxidative Stress By Modified and Conjugated CNPs In Vitro Delayed and incomplete healing of cutaneous wounds is a common complication that affects patients suffering from diabetes. Unfortunately, the mechanisms responsible for the poor healing of these impaired wounds are still not fully understood. Previous studies have demonstrated that impaired healing in diabetic skin wounds may result from an increased inflammatory response during the first week following injury leading to chronic inflammation and impaired healing. The normal physiological response to injury is the release of cytokines and other inflammatory mediators that stimulate the recruitment of inflammatory cells and proliferation of fibroblasts and endothelial cells crucial for wound repair. Recent reports indicate that IL-6 and IL-8 are two cytokines that play a major role in the endogenous response to injury. These two cytokines are principally secreted by monocytes, fibroblasts, as well as endothelial cells and other inflammatory cells.

In the skin, fibroblasts constitute the major synthesizers of the extracellular matrix (ECM) components including collagen and are considered as the one of the most important cell types for tissue repair. Following the initial inflammatory phase, fibroblasts migrate to the wound site where they proliferate and secrete ECM to promote wound closure. In vitro studies of cultured fibroblasts have shown that they can also express inflammatory genes such as IL-6 and IL-8, which may amplify the inflammatory response if not properly suppressed. However, in diabetic wounds, the levels of these proinflammatory cytokines are upregulated resulting in an increased influx of inflammatory cells to the wound area thereby forming a vicious cycle of persistent and chronic inflammation.

In in vitro studies, skin fibroblasts from 12 week-old diabetic mice (BKS.Cg-Dock7m+/+Leprdb/J mice (Db⁻/Db⁻)) and age-matched non-diabetic heterozygous littermates (C57BKS mice (Db⁺/Db⁻)) were isolated. These cells were cultured and expanded. Total RNA was extracted from these cells and the gene expression of inflammatory regulatory genes analyzed by real time PCR. This data demonstrates that diabetic fibroblasts have increased production of the proinflammatory cytokines IL-6 and IL-8/MIP2 in vitro (FIGS. 18A-18B).

Figure 19A:
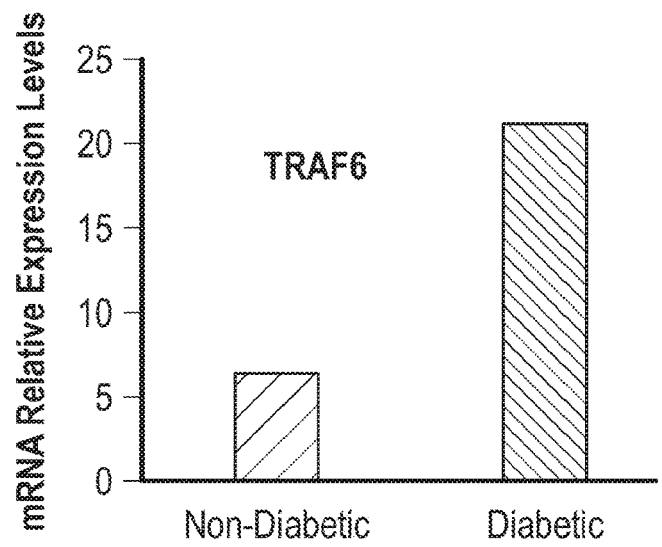
FIGS. 19A-19C are graphs illustrating increased in vitro expression of TRAF6 (FIG. 19A), IRAK1 (FIG. 19B), and NFκB (FIG. 19C) in diabetic fibroblasts relative to non-diabetic fibroblasts.
Figure 19B:
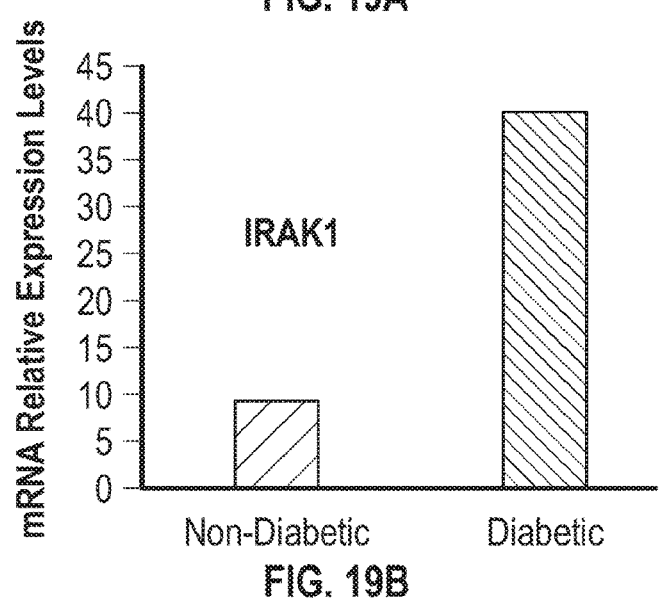
Figure 19C:
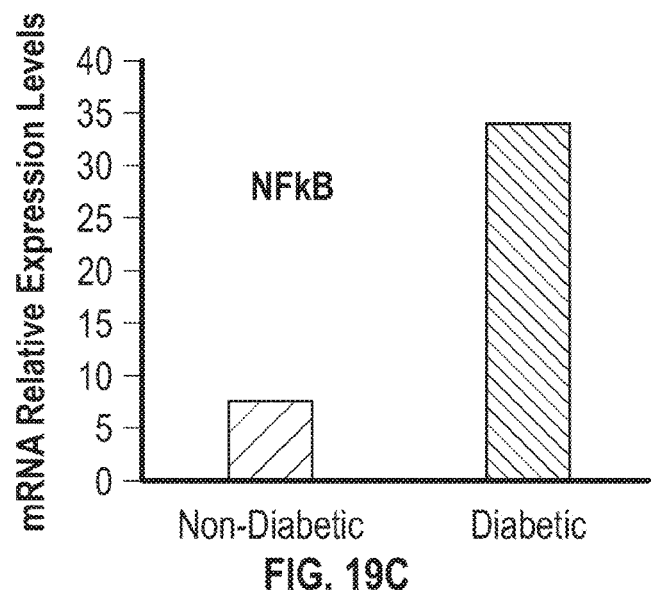

The production of IL-6 and IL-8 is regulated by the NFκB signaling pathway. Increased gene expression of the NFκB co-activators, TRAF6 and IRAK1, results in increased expression of NFκB leading to increased IL-6 and IL-8 gene expression. TRAF6 and IRAK1 gene expression, as well as the expression of NFκB in diabetic versus non-diabetic fibroblasts was examined. Diabetic fibroblasts had increased expression of TRAF6 (FIG. 19A) and IRAK1 (FIG. 19B), as well the downstream signaling molecule NFκB (FIG. 19C), compared to nondiabetic fibroblasts.

Figure 20:
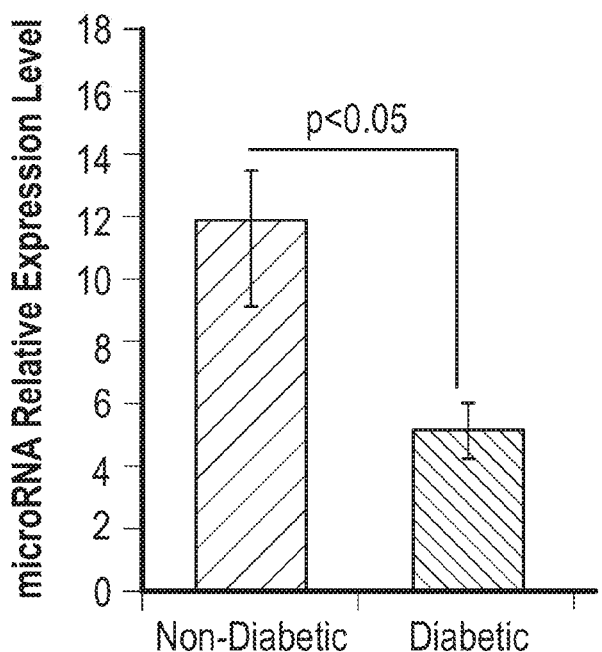
FIG. 20 is a graph illustrating the decreased miR-146a in diabetic fibroblasts relative to non-diabetic fibroblasts.

Another layer of regulation in the proinflammatory signaling pathway is at the level of microRNAs. In particular, microRNA-146a (miR-146a) acts as a brake on the inflammatory response by targeting TRAF6 and IRAK1 mRNA for suppression/degradation and thus decreasing NFκB signaling. The expression of miR-146a in diabetic versus non-diabetic fibroblasts was examined. Diabetic fibroblasts produce significantly less miR-146a (FIG. 20), which, without wishing to be bound by theory, may explain the increased NFκB signaling and proinflammatory gene expression observed in these cells.

Figure 21:
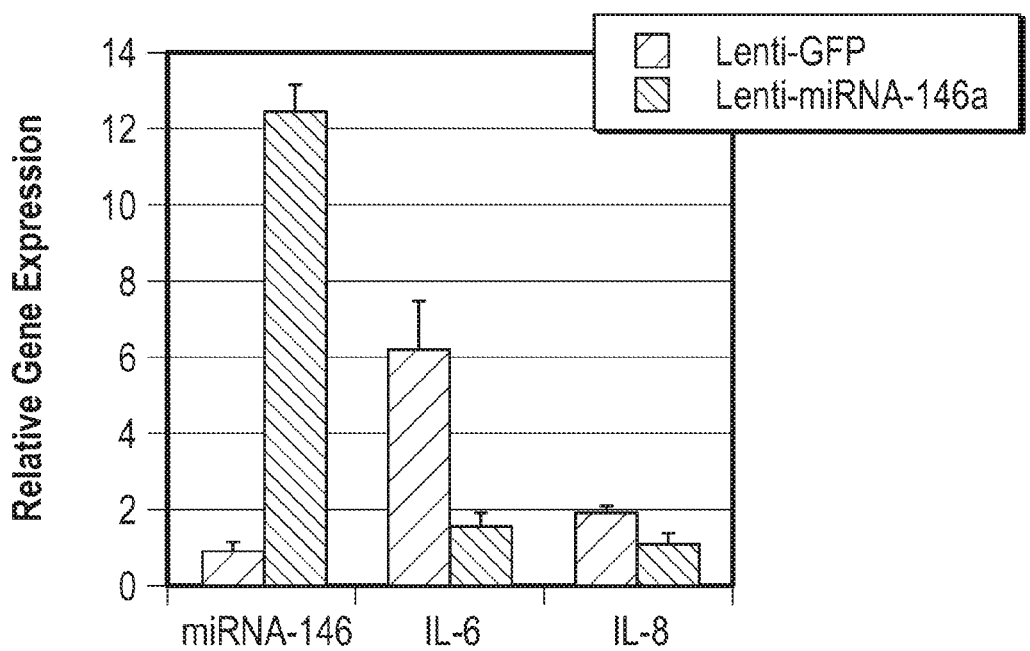
FIG. 21 is a graph illustrating that overexpression of miRNA-146a represses IL-6 and IL-8 target genes. From left to right, the chart provides the relative gene expression of Lenti-GFP followed by Lenti-miRNA-146a for each measurement (e.g., miRNA-146a, IL-6, and IL-8).

In another set of studies, the ability of lentiviral-mediated overexpression of miR-146a to decrease gene expression of the downstream proinflammatory cytokines IL-6 and IL-8/MIP2 was examined. 109 pfu of a lentivirus containing the miR-146a transgene was used to transfect 293 cells. A lentivirus containing the green fluorescent protein (GFP) was used as a control. Lentiviral mediated overexpression of miR-146a significantly reduced the expression of IL-6 and IL-8 in these cells (FIG. 21). These results show that manipulation of miR-146a levels can directly affect the levels of the pro-inflammatory cytokines IL-6 and IL-8.

This in vitro data demonstrates that diabetic fibroblasts have a phenotype that is consistent with increased proinflammatory signaling that promotes increased proinflammatory cytokine production and thus provides a model for use in screening and optimization of CNP conjugates.

In some embodiments, engineered and miR-146a-conjugated CNPs described herein correct the diabetic fibroblast phenotype resulting in decreased proinflammatory signaling, decreased proinflammatory cytokine production, and decreased oxidative stress. To show this effect, fibroblasts can be isolated from diabetic and non-diabetic mice. Diabetic and non-diabetic fibroblasts can be divided into five experimental groups with six timepoints (3, 6, 12, 24, 36, and 48 hours), to determine the most efficient formulation in correcting the diabetic pro-inflammatory phenotype. The treatment groups can include: Group 1: Vehicle Control; Group 2: Lenti-miR-146a (109 pfu); Group 3: CNPs; Group 4: Engineered-CNPs; Group 5: Engineered and Conjugated CNPs. Groups 3, 4, and 5 can test 3 different doses of the CNP constructs. At 3, 6, 12, 24, 36, and 48 hours following treatment, fibroblasts can be harvested for total cellular RNA isolation, protein isolation, and oxidative stress assays. The supernatants can be collected for determination of proinflammatory cytokine protein production by ELISA. Real-time PCR can be used to examine gene expression of miR-146a, its direct targets TRAF6 and IRAK, and the gene expression of the downstream inflammatory mediators NFκB, IL-6, and IL-8. Real-time PCR can also be performed for the oxidant enzyme NADPH oxidase (NOX2), which is involved in catalyzing the production of superoxide from oxygen and NADPH, and the antioxidant enzyme glutathione peroxidase-4 (GPX4), which reduces hydroperoxides and reduces oxidative stress. Protein levels can be quantified by Western blot analysis using commercially available antibodies.

ROS levels can be assessed using the OxiSelect™ Intracellular ROS Assay from Cellbiolabs Inc., which provides a sensitive method to detect total ROS. This assay employs a fluorogenic cell permeable probe, DCFH-DA. In the presence of ROS and RNS, the DCFH is rapidly oxidized to the highly fluorescent DCF. Fluorescence is read on a standard plate reader with adequate filters. A two-tailed Student's t-test can be used to determine statistical significance between two conditions. ANOVA with an appropriate post hoc test may be used for multiple comparisons. P values≤0.05 are be considered significant.

In some embodiments, CNP treatment by itself may decrease oxidative stress in diabetic fibroblasts and may increase miR-146a gene expression resulting in dowregulation of NFκB, IL-6, and IL-8. Lentiviral mediated overexpression of miR-146a may also increase the endogenous levels of miR-146a in both diabetic and non-diabetic fibroblasts and decrease inflammatory signaling. Treatment with CNPs coated with HA may also have anti-inflammatory effects due to the known anti-inflammatory properties of HA and also decrease ROS levels.

In some embodiments, engineering and conjugation of CNPs with miR-146a have a synergistic effect on suppression of the inflammatory response and decrease in oxidative stress, greater than the sum of the individual treatment effects. Based on the dose response and analysis of engineered and conjugated CNP treatment, the optimum formulation for use in the in vivo experiments described below will be determined to reduce inflammation, decrease oxidative stress, and correct the diabetic wound healing impairment. Lack of synergy between the CNP, the engineered coating, and the conjugated microRNA may be addressed through the modulation of the valence state of the CNP, the use of alternative coating molecules such as collagen or fibrinogen, or altered conjugation strategies. Potential toxicity of the nanoparticles can be addressed with alternative dosing strategies.

Example 3

Figure 10A:
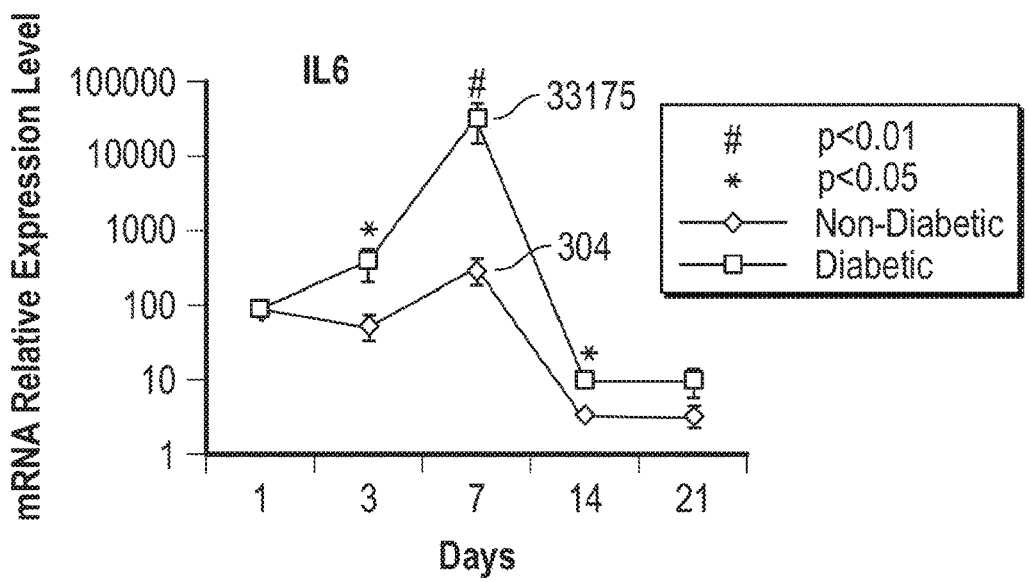
FIGS. 10A-10B are graphs illustrating increased gene expression of proinflammatory cytokines in diabetic wounds relative to non-diabetic wounds.
Figure 10B:
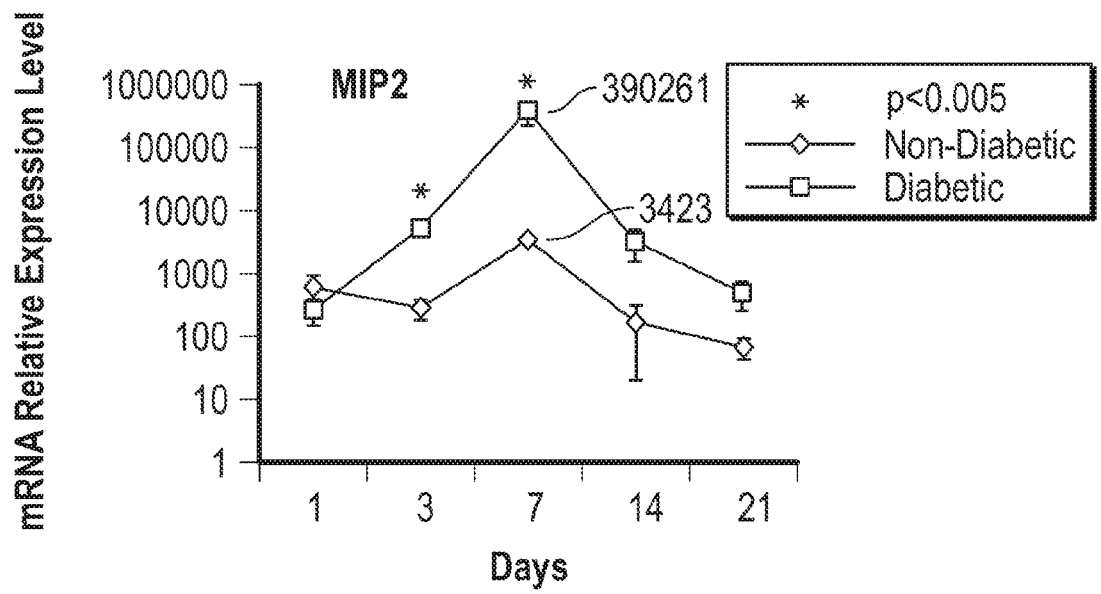
Figure 12A:
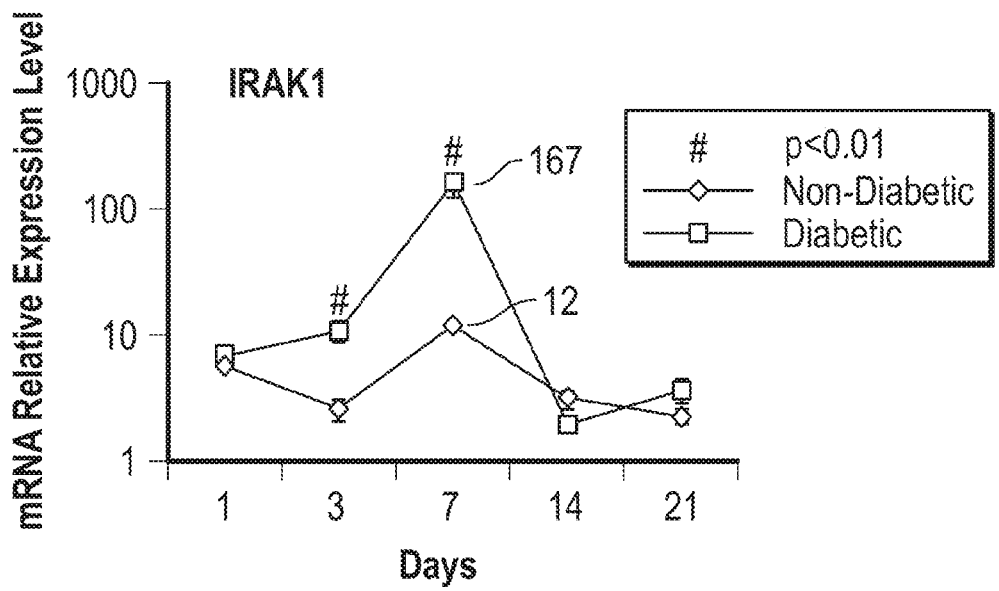
FIGS. 12A-12B are graphs illustrating the increased expression of proinflammatory signaling pathways in diabetic wounds.
Figure 12B:
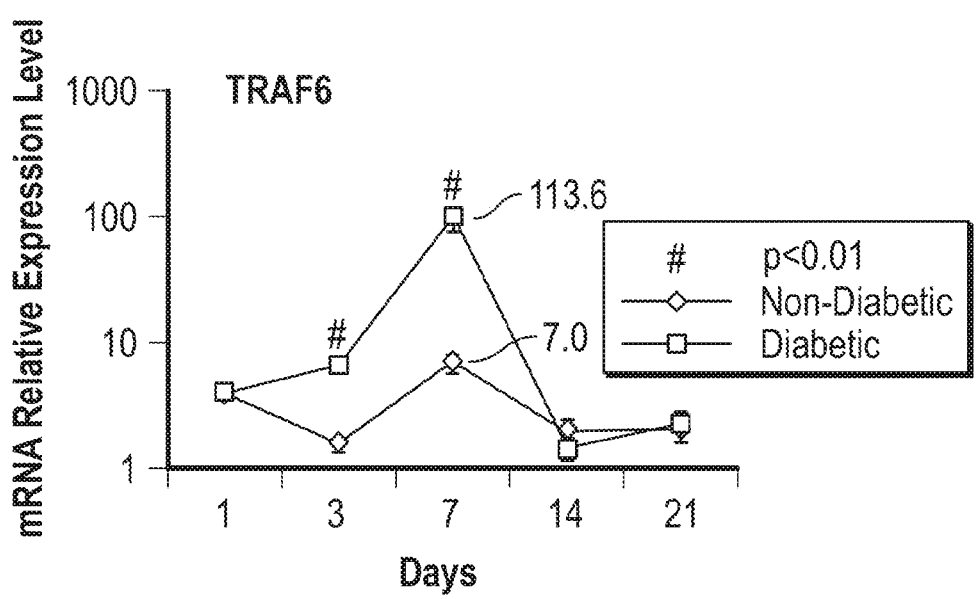
Figure 22:
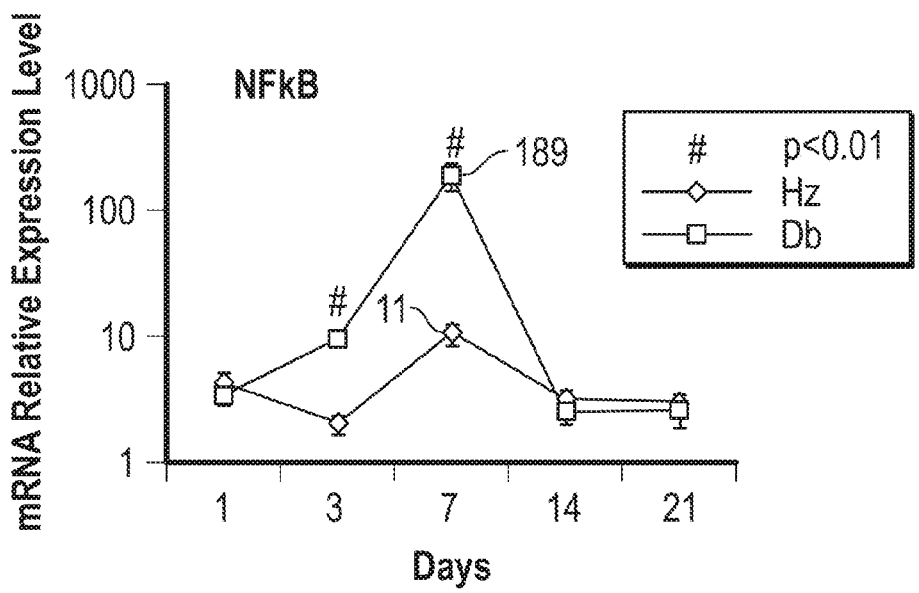
FIG. 22 is a graph illustrating increased NFκB in diabetic wounds relative to non-diabetic wounds.

Testing of Modified and Conjugated CNPs in a Murine Model of Impaired Diabetic Wound Healing and Investigation of the Mechanisms of the Correction of the Wound Healing Impairment The wound healing process is regulated by a large variety of different inflammatory mediators and cytokines. In spite of current advances in the understanding of mechanisms of wound healing, treatment of impaired diabetic skin wounds remains limited. Any advancement in the treatment of chronic diabetic wounds will require greater understanding of their inability to heal. The present technology provides such an advancement. Diabetic skin wounds are characterized by an upregulated and sustained inflammatory response. Data presented herein demonstrates that diabetic wounds have increased inflammation (FIGS. 9A-9B) due to increased expression of the pro-inflammatory cytokines, IL-6 and IL-8/MIP2 (FIGS. 10A-10B). IL-6 and IL-8/MIP2 gene expression is upregulated by NFκB, which is shown to be increased in diabetic wounds (FIG. 22). NFκB gene expression is regulated, in part, by IRAK1 and TRAF6, which is also shown to be elevated in diabetic wounds (FIGS. 12A-12B).

Figure 23:
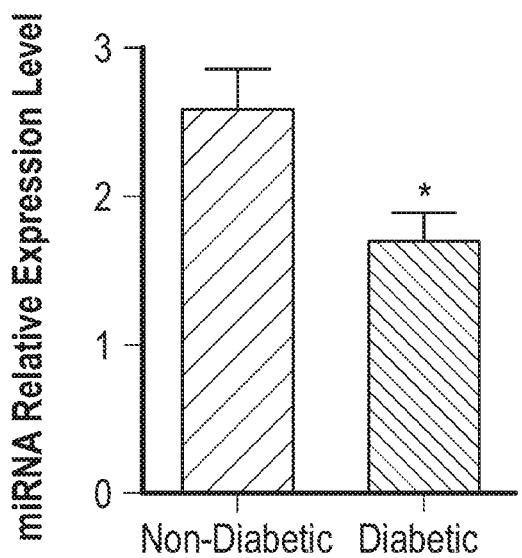
FIG. 23 is a graph illustrating decreased miR-146a in human diabetic skin at baseline.

MicroRNAs have emerged as regulators of gene expression. In particular, miR-146a is an important brake on inflammation by targeting and suppressing IRAK1 and TRAF6. As demonstrated herein, miR-146a gene expression is also decreased in murine diabetic wounds (FIG. 11), thus promoting increased pro-inflammatory signaling through NFκB. As demonstrated herein, human diabetic skin has decreased miR-146a expression at baseline, compared to non-diabetic skin (FIG. 23), which, without wishing to be bound by theory, may explain the increased and chronic inflammatory response seen in human diabetic wounds clinically.

Increased and persistent inflammation results in increased reactive oxygen species (ROS) and increased oxidative stress. ROS generated by the inflammatory response is critical following injury and if persistent, may contribute to impaired healing. ROS include hydrogen peroxide ($H_2O_2$), superoxide radicals, hydroxyl radicals and peroxynitrates, which can alter the function of proteins, lipids, and even DNA. These alterations disrupt the normal functioning of the cells leading to significant dysfunction at tissue level.

Diabetic mice (BKS.Cg-Dock7m+/+Leprdb/J mice (Db$^-$/Db$^-$)) and age-matched non-diabetic heterozygous littermates (C57BKS mice (Db$^+$/Db$^-$)) were used in the studies described herein. Prior to any procedure, the mice were anesthetized with inhaled isofluorane. The dorsal skin of the mice was shaved, depilatated, and cleaned with ethanol. For studies of murine diabetic fibroblasts, 12-week-old diabetic (Db/Db) and non-diabetic (Db/+) mice were euthanized and dorsal skin harvested and fibroblasts isolated and cultured. For the studies of murine diabetic wounds, an 8-mm full thickness wound was created on the flank of the 12-week-old diabetic and non-diabetic mice through the panniculus carnosus using a dermal punch and covered with Tegaderm dressing. The wounds were treated with a dose response curve of the miRNA-146a-CNP conjugate, and lenti-miR-146a, CNPs, or vehicle served as controls. At 1, 3, 7, 14, 21, or 28 days after wounding, the animals were euthanized and the wound and surrounding tissue was harvested.

Figure 24:
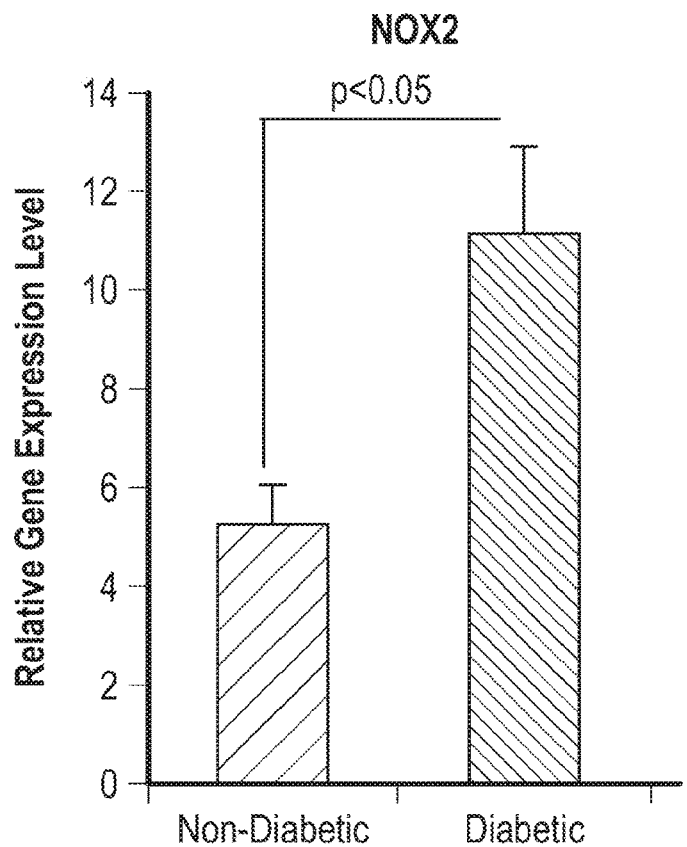
FIG. 24 is a graph illustrating increased NOX2 expression in diabetic wounds at day 7 relative to non-diabetic wounds.
Figure 25:
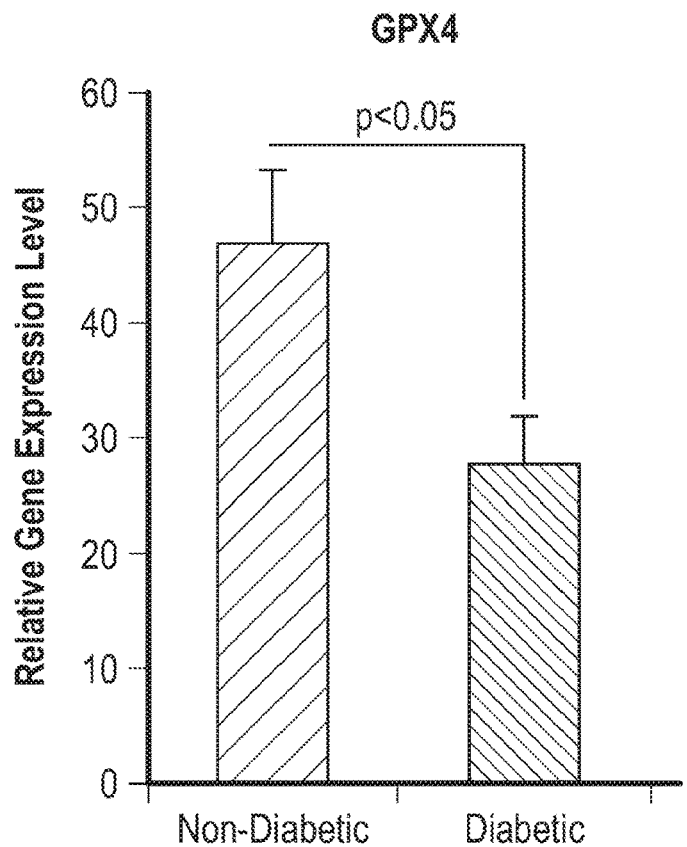
FIG. 25 is a graph illustrating decreased GPX4 expression in diabetic wounds at day 7 relative to non-diabetic wounds.

Measurements of oxidative stress include examining the different reactive oxygen species (ROS), as well as the enzymes responsible for their generation and degradation. Data shown in FIG. 24 reveals the gene expression of enzymes involved in the generation of superoxides in diabetic and non-diabetic subjects. FIG. 24 demonstrates the gene expression of the inducible NADPH oxidase (NOX2), which is involved in catalyzing the production of superoxide from oxygen and NADPH. In the diabetic wounds, NOX2 was significantly increased at 7 days compared to non-diabetic wounds, consistent with increased oxidative stress. In addition to examining factors involved in the generation of ROS, the gene expression of glutathione peroxidase 4 (GPX4), which is an antioxidative stress enzyme that scavenges hydrogen peroxide, organic hydroperoxides, and lipid peroxides was examined. Diabetic wounds had decreased expression of GPX4 at Day 7 after wounding (FIG. 25).

Figure 26:
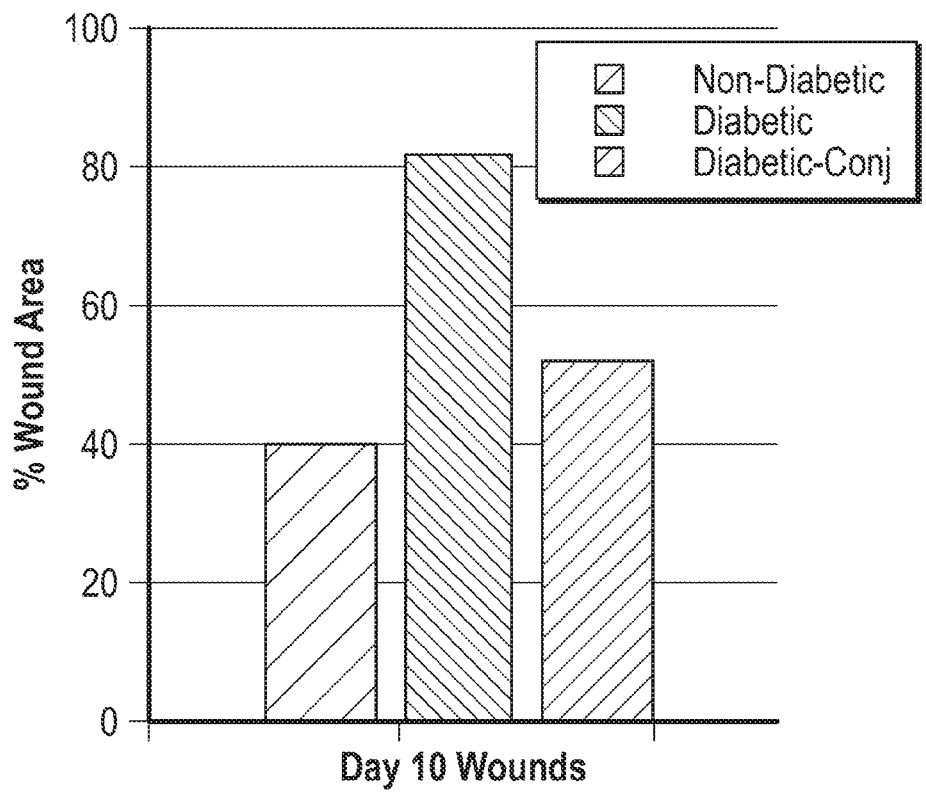
FIG. 26 is a graph illustrating the correction of the diabetic wound healing impairment with conjugated CNPs.
Figure 27:
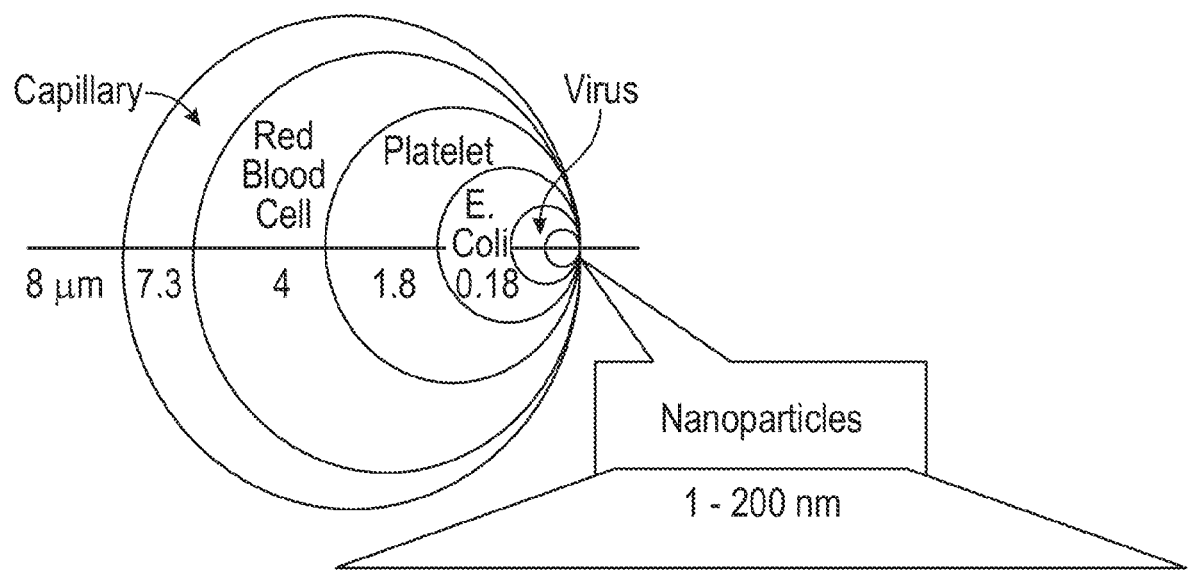
FIG. 27 is a drawing depicting the size of a cerium oxide nanoparticle (nanoceria).

The effect of miR-146a conjugated-CNPs on wound closure was examined. At 7 and 10 days, diabetic wounds treated with miR-146a conjugated CNPs at the time of wounding (intradermal injection of 1 μg miR-146a-CNP conjugate) demonstrated a dramatic decrease in the wound area (FIG. 26). This data demonstrates that conjugated CNPs can be used as a treatment in in vivo experiments and clinical applications. It also shows that conjugated CNPs are effective in reducing the diabetic wound size by approximately 40% compared to control-treated, same-size diabetic wounds.

The data described above demonstrate that diabetic skin has a significant dysregulation of the inflammatory response to injury resulting in increased oxidative stress and impaired healing. These studies also demonstrate that the impaired inflammatory response in diabetic skin is due to abnormal posttranscriptional regulation of NFκB levels. Data disclosed herein indicates that alterations of regulatory microRNAs in diabetes play a significant role in the abnormal inflammatory response and oxidative stress in diabetic skin at baseline and following injury. In some embodiments, engineered and conjugated CNPs are synergistic in the correction of the diabetic wound healing impairment by decreasing inflammation, scavenging ROS, and decreasing oxidative stress.

Figure 30:
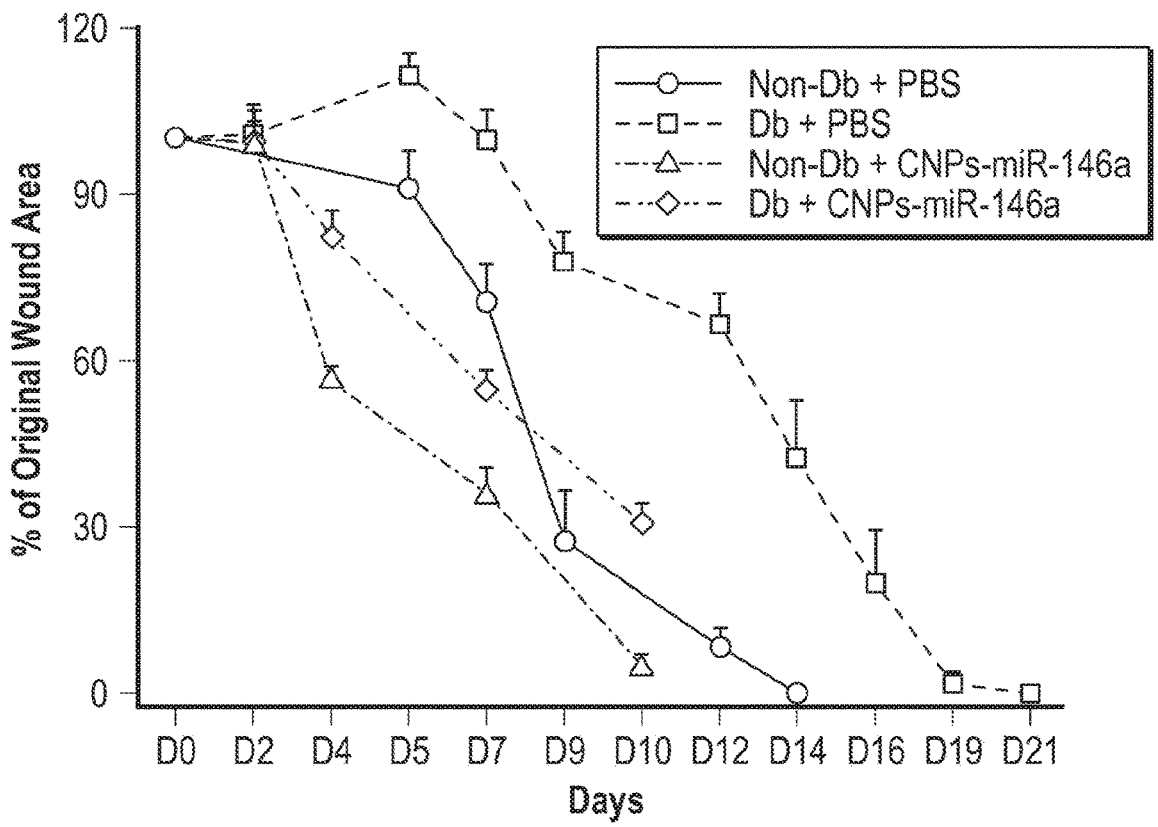
Figure 31:
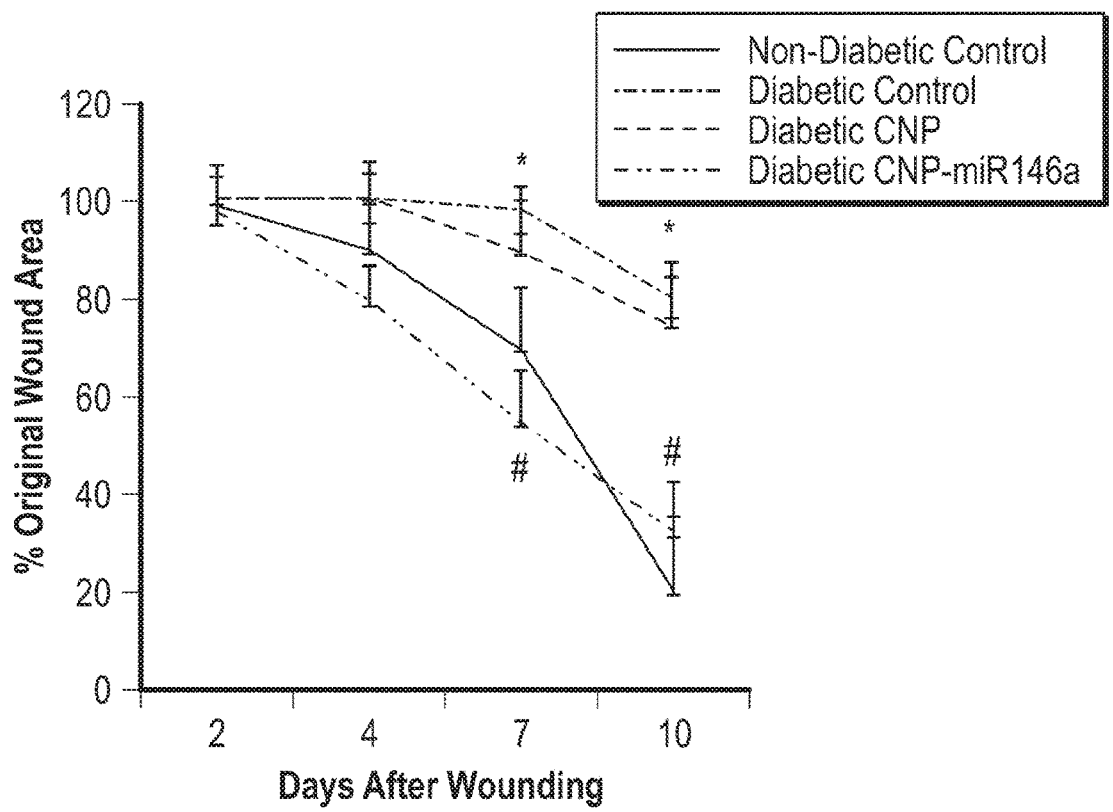
Figure 32A:
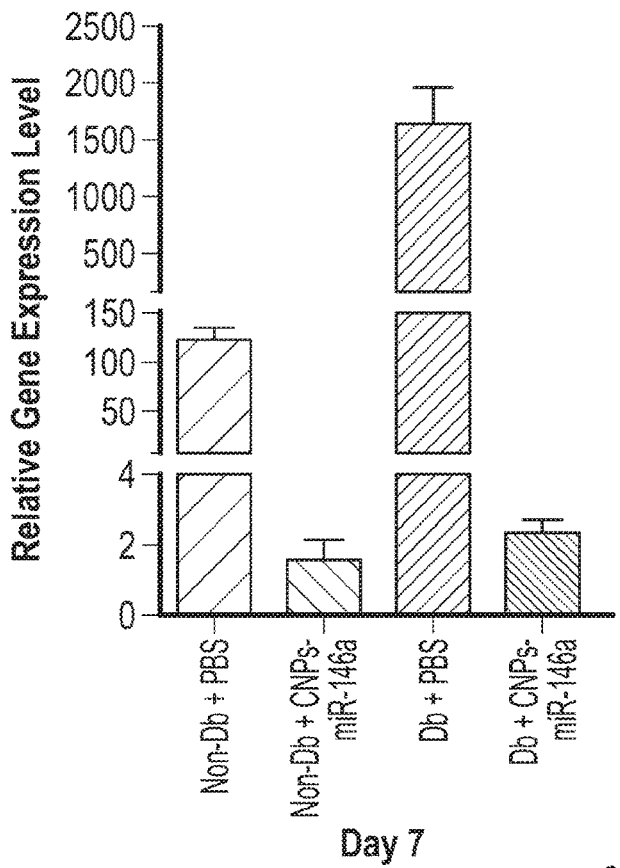
FIGS. 32A-32B are graphs illustrating relative gene expression levels for IRAK1 (FIG. 32A) and TRAF 6 (FIG. 32B) in wounds from diabetic and non-diabetic mice with and without CNP-miR146a at 7 days.
Figure 32B:
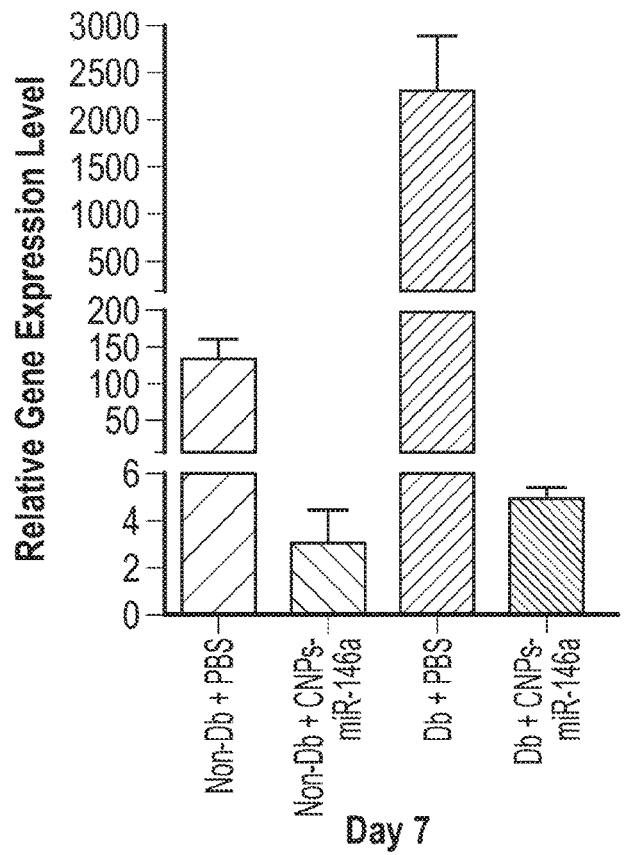
Figure 33:
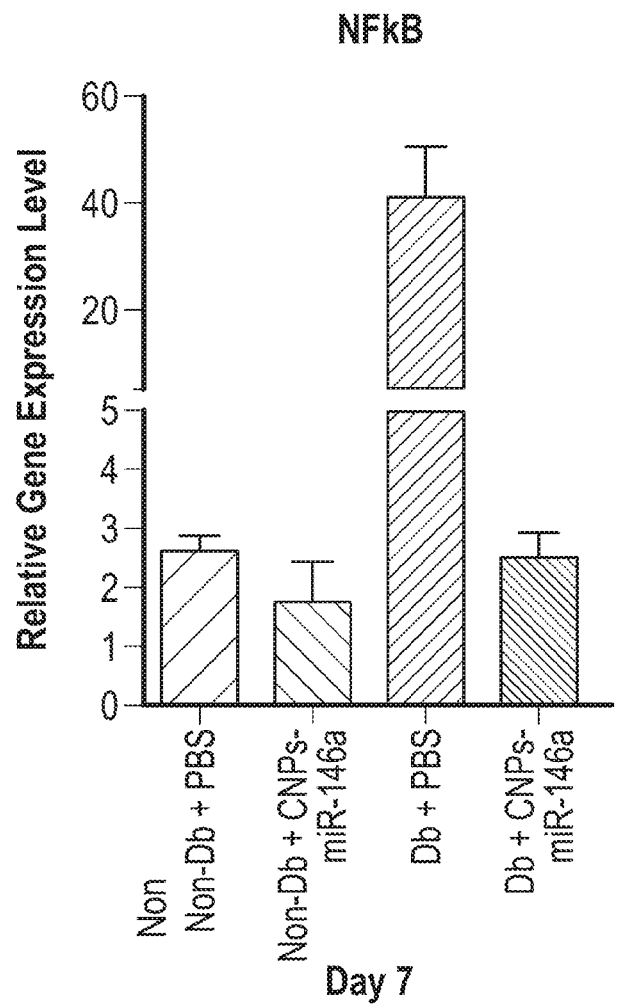
FIG. 33 is a graph illustrating relative gene expression levels for NFκB in wounds from diabetic and non-diabetic mice with and without CNP-miR146a at 7 days.

Efficacy of the engineered and conjugated CNPs is demonstrated using 8 mm wounds created on the flank of diabetic and non-diabetic mice (FIGS. 29A-29B and 30). Wounds were treated with a dose response curve of a candidate compound. Lenti-miR-146a, CNPs, or vehicle serve as controls. At 1, 3, 7, 14, 21, and 28 days after wounding, tissue was processed for histology, immunohistochemistry, total cellular RNA, protein, and protein activity analysis. Real-time PCR was used to assess NFκB, TRAF6, IRAK1, IL-6, IL-8, and miR-146a gene expression. Western blot was used to assess NFκB, IL-6, and IL-8 protein production. FIGS. 32A and 32B show increased IRAK-1 and TRAF6 in diabetic wounds at 7 days. Treatment with CNP-miR146a resulted in a significant decrease in IRAK-1 (FIG. 32A) and TRAF-6 (FIG. 32B) at 7 days. FIG. 33 shows increased NFκB in diabetic wounds at 7 days. Treatment with CNP-miR146a resulted in a significant decrease in NFκB at 7 days (FIG. 33). FIG. 34 shows increased IL-6 and IL-8 in diabetic wounds at 7 days. Treatment with CNP-miR146a resulted in a significant decrease in IL-6 and IL-8 at 7 days (FIG. 34).

Figure 35A:
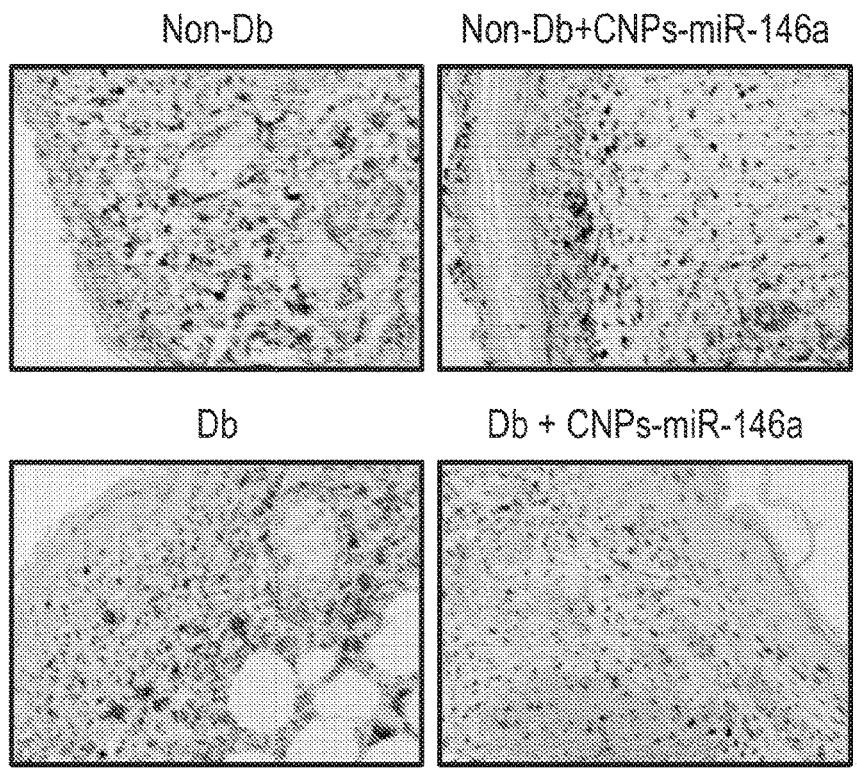
Figure 35B:
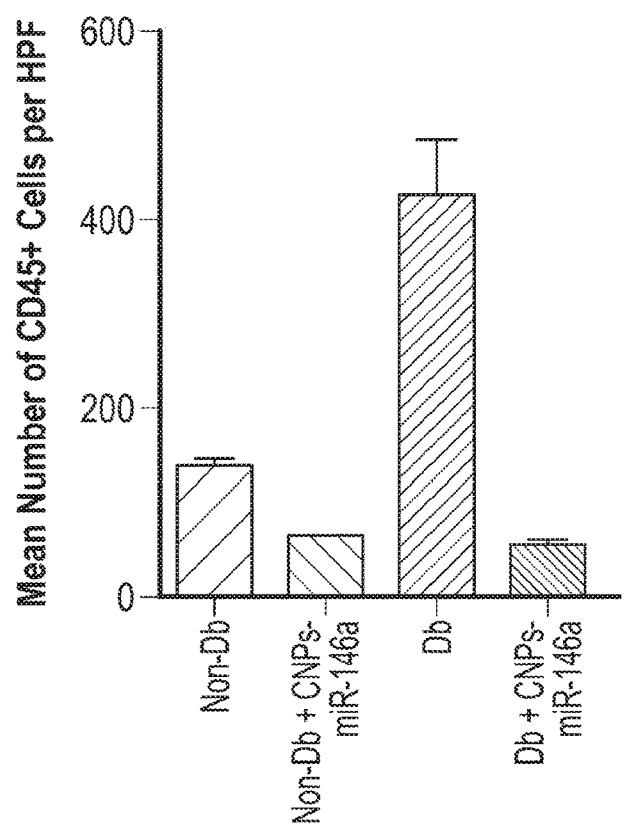
Figure 36:
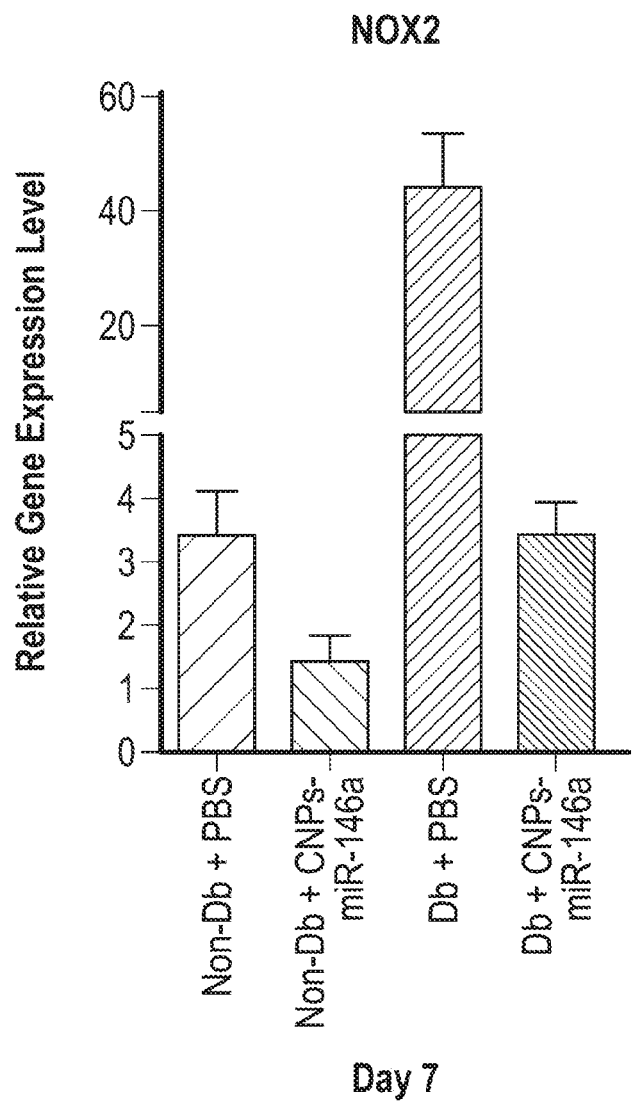
FIG. 36 is a graph illustrating relative gene expression levels for NOX2. This demonstrates increased oxidative stress in untreated wounds and decreased oxidative stress with CNP conjugate treatment to normal wound levels.

Tissue architecture is assessed by histology using H&E and Mason trichrome staining. In order to determine the absolute number and type of inflammatory cells in the wound, quantitative histology was performed using immunohistochemistry for CD45, the common leukocyte antigen. Diabetic wounds demonstrated significantly increased inflammatory cells (FIGS. 35A-35B). Treatment of diabetic wounds with CNP-miR146a resulted in a significantly decreased inflammatory cell infiltrate (FIGS. 35A-35B). The major enzyme responsible for increased oxidative stress by inflammatory cells is NADPH oxidase (NOX2). FIG. 36 shows the real-time PCR analysis of diabetic and non-diabetic wounds at 7 days for NOX2. Diabetic wounds demonstrate significantly increased NOX2, consistent with increased oxidative stress, compared to non-diabetic wounds. Treatment with CNP-miR146a resulted in a significant decrease in NOX2 and oxidative stress at 7 days (FIG. 36).

Figure 37:
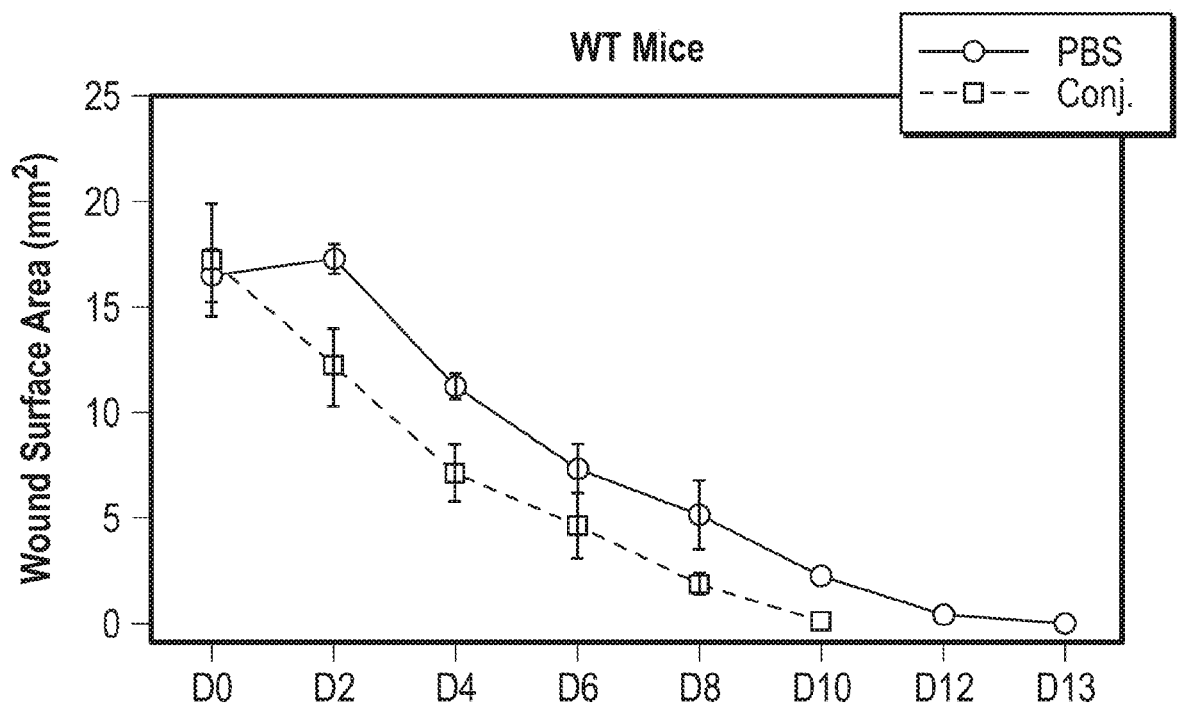
FIG. 37 is a graph illustrating the wound surface area over time for normal mice receiving PBS (Control, top line at Day 2) or CNPs-miR-146a (Conj., bottom line at Day 2). Treatment with CNP-miR-146a resulted in accelerated normal wound healing.

FIG. 37 shows the rate of wound closure over time in normal mice following treatment with PBS (control) or CNP-miR146a. CNP-miR146a treatment results in increased rate of wound closure in normal mice.

Figure 38:
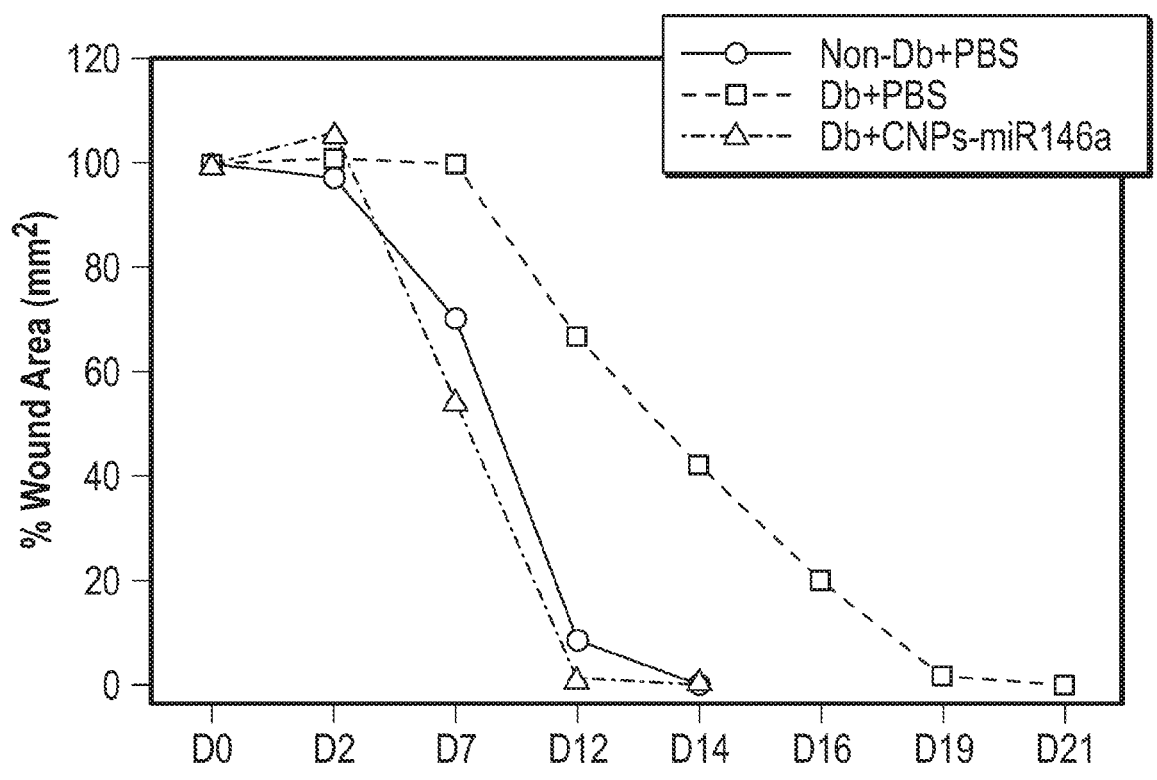
FIG. 38 is a graph illustrating the wound surface area over time for diabetic (Db) and non-diabetic (Non-Db) wounds treated with PBS (Control) or receiving CNPs-miR-146a. Treatment with CNP-miR146a corrected diabetic healing rates to that of non-diabetic wounds. At day 2, the plots proceed as follows from top to bottom: Db+CNPs-miR-146a; Db+PBS; and Non-Db+PBS.

FIG. 38 shows the rate of wound closure over time in diabetic and non-diabetic wounds following treatment with PBS (control) or CNP-miR146a. Diabetic control wounds demonstrate a significant delay in the rate of closure and the time to closure compared to non-diabetic wounds. Treatment of diabetic wounds with CNP-miR146a corrected the rate of closure and time to closure to that seen in normal wounds.

In addition, photographs were taken with a Nikon camera using a ruler for each image. ImageJ software (National Institutes of Health, Bethesda, MD) and used to calculate the wound area of each mouse at every timepoint and wound area was plotted as a function of time.

miR-146a expression is increased and ROS levels are decreased with miR-146a-conjugated CNP treatment in diabetic wounds. This is associated with a significant decrease in inflammatory cell infiltration and oxidative stress, improved healing, and faster wound closure. Specifically, a decrease in the levels of NFκB, IRAK1, TRAF6, IL-6, and IL-8 is observed. There has been no effective treatment that can target and decrease inflammation and reduce oxidative stress directly at the wound site. The approach of combining gene therapy together with Nanotherapy by using miR-146a-conjugated CNPs, as described herein, is a novel approach. Moreover, this therapy can be readily transferred and applied to patients as it is safe and can be applied locally to the wound. If the dosing regimen for the nanoparticles is not sufficient to effectively reduce inflammation and oxidative stress in a given application, a second and/or a third additional dose at day 2 and day 3 following wounding can be applied.

Example 4

Figure 39:
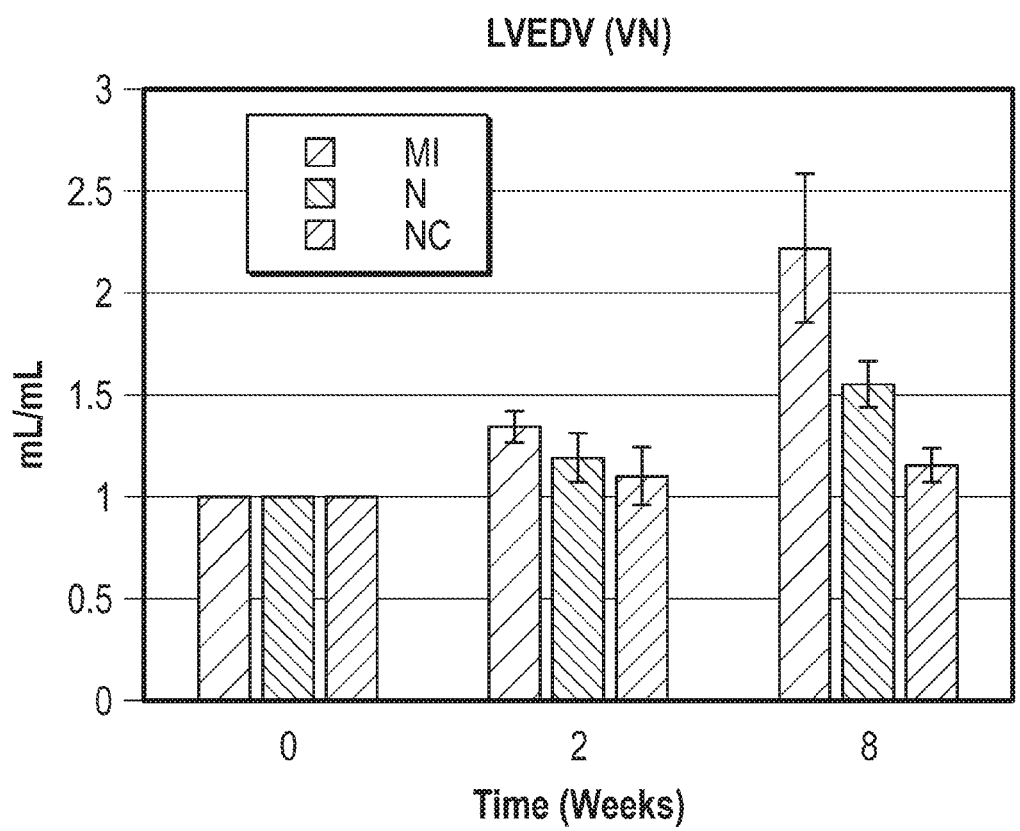
Figure 40A:
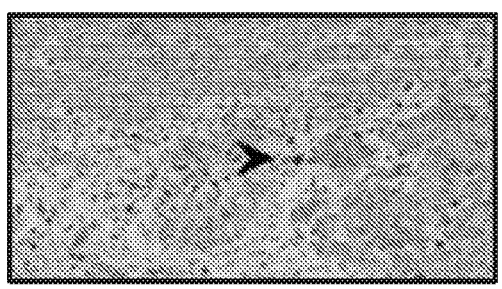
FIGS. 40A-40D are images comparing resolution of inflammation and apoptosis in fetal infarcts as compared to adult infarcts in sheep.
Figure 40B:
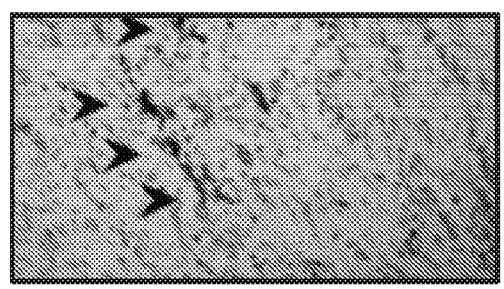
Figure 40C:
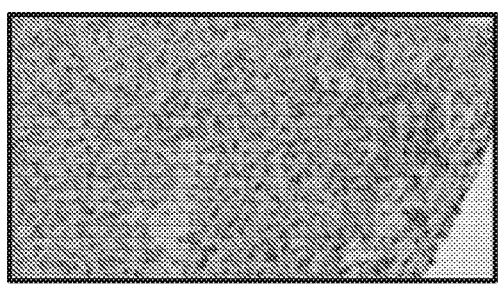
Figure 40D:
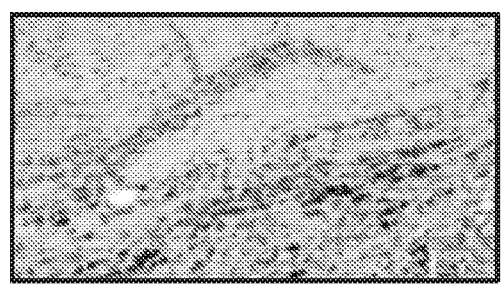

MicroRNA Conjugates with Nanoceria Decrease Inflammation and Oxidative Stress, and Promote Healing While Preventing Adverse Remodeling FIG. 39 shows the results of treatment of myocardial infarction (MI) with microRNA/nanoceria conjugate at 2 weeks and 8 weeks based upon LVEDV in an adult sheep MI model. Treatment with nanoceria/microRNA conjugate (NC; 30 µg direct injection into infarct) reduced ventricular dilation over untreated replicates (MI) at 8 weeks post-infarction (FIG. 39). The results observed with the conjugate at 8 weeks evidenced a ventricular dilation closest to the replicates at the t=0 timepoint. Treatment with an equivalent dose of nanoceria alone (N) also resulted in reduced ventricular dilation over untreated replicates (MI) at 8 weeks post-infarction (FIG. 39). However, treatment with nanoceria/microRNA conjugate (NC) was able to reduce ventricular dilation over treatment with nanoceria alone at 8 weeks post-infarction (FIG. 39), highlighting the synergistic effect of treatment with the nanoceria/microRNA conjugate. Similar results were observed at the two-week time point, although the effects were not as dramatic (FIG. 39). This implicates the continued damage to heart muscle that evolves with time, and the ability of the nanoceria/microRNA conjugate to significantly mitigate this damage.

As previously discussed, FIG. 39 is a histogram illustrating that the microRNA/nanoceria conjugate improves healing following myocardial infarction. MI=untreated myocardial infarction (angled black line shading in the bar); N=treatment with nanoceria alone (solid black shading in the bar); NC=treatment with nanoceria/microRNA conjugate (black with white dot shading in the bar). The histogram represents n of at least 5 for each group or about 15 adult sheep infarcts.

LVEDV refers to "left ventricular end-diastolic volume" and is a measure of ventricular dilation after myocardial infarction (MI), which leads to heart failure. No treatment (MI) results in dilation, which increases at 8 weeks following MI. Nanoceria (N) decreased dilation at 2 weeks and 8 weeks post-MI. MicroRNA/Nanoceria conjugates further decreased this dilation.

Over one million Americans sustain an acute myocardial infarction (MI) each year and over 5 million Americans suffer from heart failure. In spite of the widespread application of reperfusion therapy for acute MI and state-of-the-art post MI pharmacotherapy, adverse ventricular remodeling after MI remains the most common cause of heart failure.

Figure 41A:
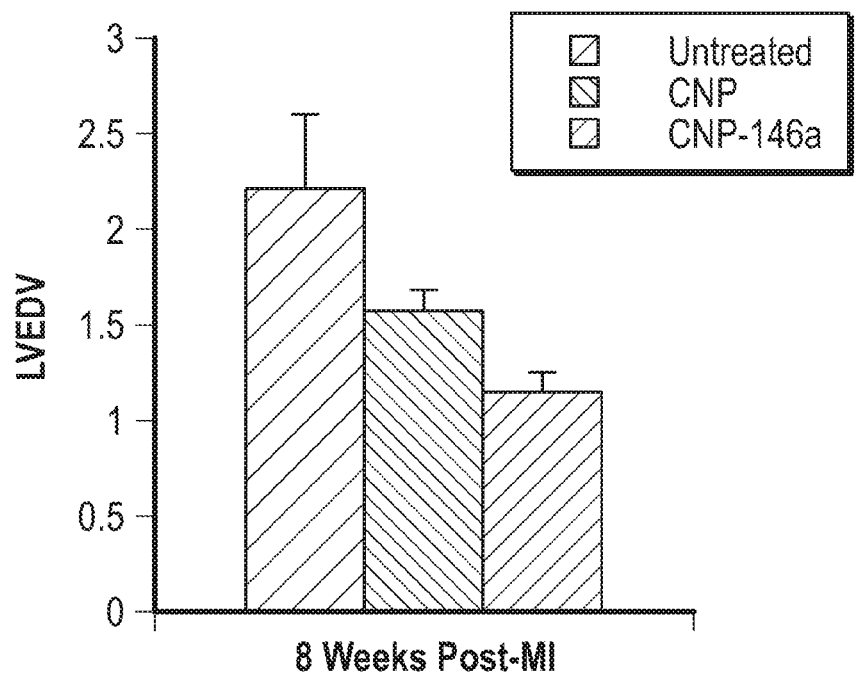
FIGS. 41A-41B are histograms. The first histogram (FIG. 41A) shows the LVEDV at 8 weeks post-MI for the indicated conditions. In the first histogram, the conditions/replicates presented are from left to right as follows: Untreated; CNP; and CNP-146a. The second histogram (FIG. 41B) shows that the persistent inflammation and apoptosis in adult infarcts is associated with increased oxidative stress at 30 days after MI, with significantly increased NOX2 gene expression. In the second histogram, the bar on the left represents the fetal replicate and the bar on the right represents the adult replicate.
Figure 41B:
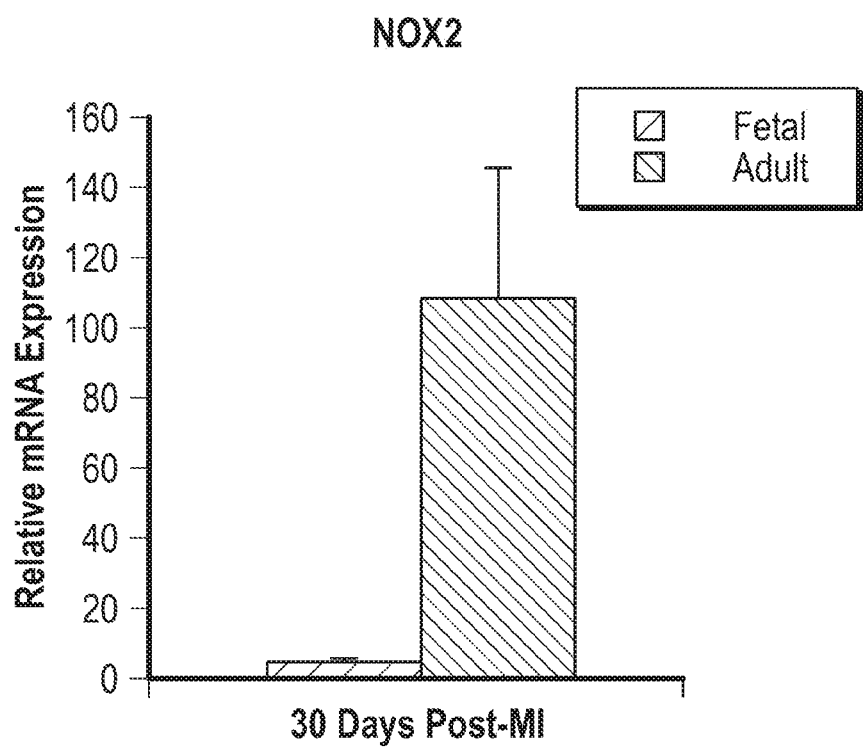

Disclosed herein is the first mammalian large animal model of cardiac regeneration following in utero MI in fetal sheep. Thirty days following the creation of a large MI by surgical ligation of the LAD, fetal sheep demonstrated restoration of a normal ejection fraction (EF) and no akinetic myocardium by echocardiography, compared to adult infarcts that demonstrate a progressive decline in function and infarct expansion. As shown in FIGS. 40A-40D, this regenerative fetal response is associated with resolution of inflammation and decreased apoptosis in the fetal infarct compared to the adult infarcts, which demonstrate persistent inflammation and apoptosis at 30 days. Persistent inflammation and apoptosis in adult infarcts is associated with increased oxidative stress at 30 days after MI, with significantly increased NOX2 gene expression (FIG. 41B).

Regulation of the inflammatory response occurs at multiple levels. At the cellular level, wound macrophage phenotype plays a central role in the initiation and resolution of the inflammatory response. Early in the response to injury, macrophages are polarized to the M1 phenotype and produce proinflammatory cytokines and stimulate the production of reactive oxygen species (ROS) to promote clearance of bacteria and debris from the wound. After the initial inflammatory phase, macrophages transition to an M2 phenotype which results in resolution of the inflammatory response and promotion of wound remodeling and closure. Increased ROS promotes proinflammatory M1 macrophage polarization and is implicated in the development of chronic inflammation through persistence of the M1 macrophage phenotype and a failure to transition to the M2 phenotype.

The inflammatory response is also regulated by proinflammatory gene expression and transcription. MicroRNAs (miR) are small noncoding RNA molecules involved in the posttranscriptional regulation of gene expression. In particular, miR-146a has been described as the "molecular brake" on the inflammatory response, by targeting and repressing the activation of the NFkB/IL-6/IL-8 inflammatory pathway.

Figure 46:
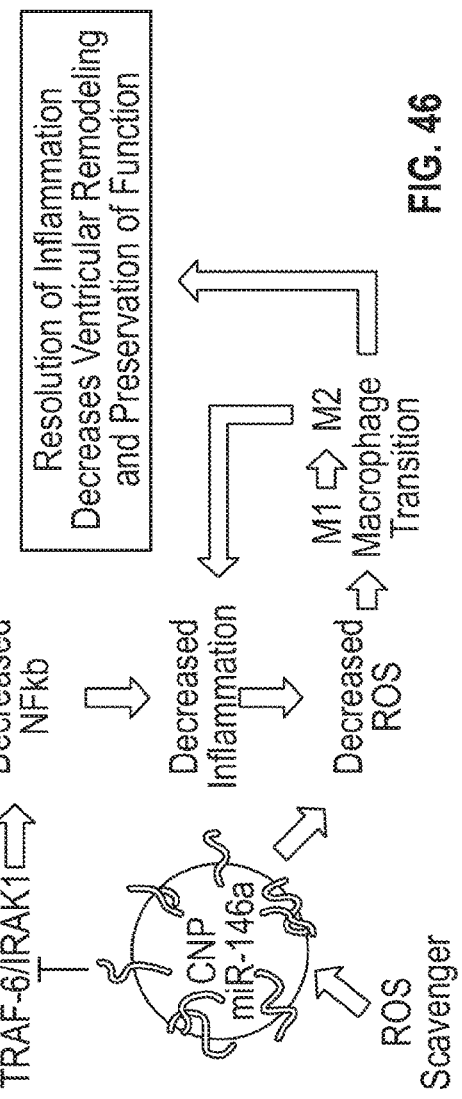
FIG. 46 is a schematic showing a proposed mode of action for the CNP-146a conjugate when used to treat MI. Overview: CNP-146a decreases ROS by direct scavenging and indirectly by decreasing inflammation. Decreased ROS leads to an M1-to-M2 macrophage transition and results in resolution of the inflammatory response, decreased ventricular remodeling, and preservation of ventricular function.

In some embodiments, the present technology relates to the development of cerium oxide nanoparticles (CNPs) that are capable of scavenging excess ROS, similar to the catalytic activity of superoxide dismutase (SOD) and catalase. In some embodiments, the present technology relates to the conjugation of these cerium nanoparticles with miR-146a, to target both ROS and the inflammatory response, and, without wishing to be bound by theory, promote the M1 (proinflammatory) to M2 (regenerative) macrophage phenotype transition to resolve the inflammatory response and improve adult infarct healing, as shown in the schematic of FIG. 46. Data presented herein demonstrates that treatment of adult infarcts with the miR-146a-conjugated CNPs of the present technology prevents adverse ventricular remodeling (FIG. 39).

Example 5

Figure 42:
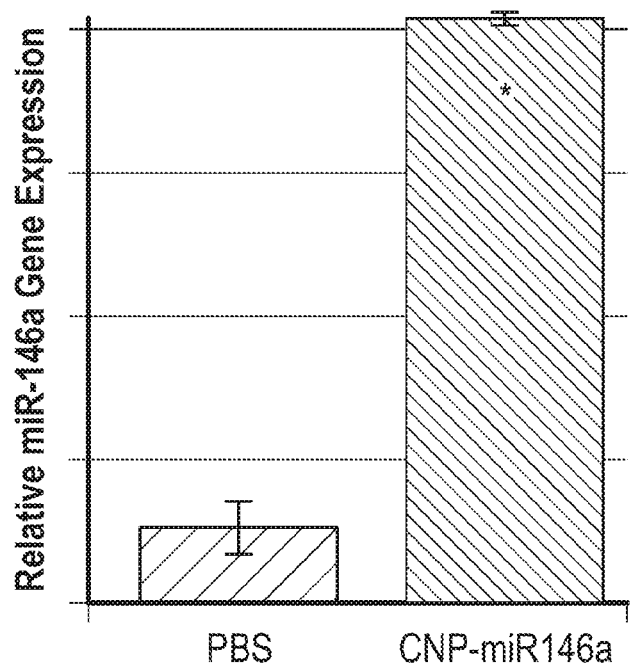

CNP-miR-146a Conjugates Uncrease miR-146a Gene Expression and Decrease Proinflammatory Cytokines in Cardiac Fibroblasts The ability of the CNP-miR146a conjugates of the present technology to increase miR-146a gene expression in vitro was examined. Adult cardiac fibroblasts were treated for 24 hours with either PBS or 1 µg CNP-miR146a and miR-146a gene expression was assessed by qPCR. Adult cardiac fibroblasts have low levels of miRNA-146a gene expression when treated with PBS; however, CNP-miR146a treatment resulted in a significant upregulation of miRNA-146a gene expression by adult cardiac fibroblasts (FIG. 42, *p<0.01).

The effect of CNP-miR146a on fibroblast IL-6 gene expression was examined. Adult cardiac fibroblasts were treated with either PBS or 1 µg of CNP-miR146a for 24 hours and IL-6 gene expression was assessed by qPCR.

Figure 43:
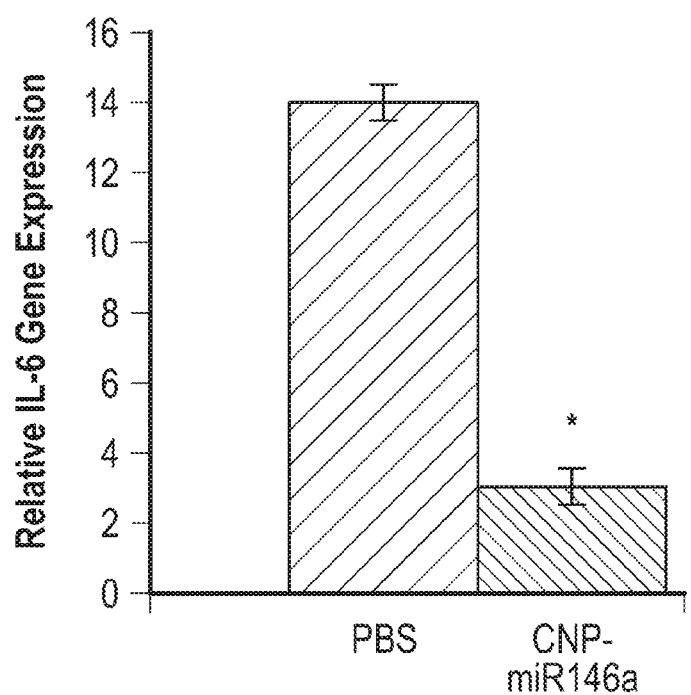

Treatment of adult cardiac fibroblasts with 1 μg of CNP-miR146a conjugate resulted in a significant decrease in IL-6 gene expression, (FIG. 43, #p<0.01).

This in vitro data demonstrates that adult cardiac fibroblasts have decreased miR146a gene expression at baseline that is consistent with increased proinflammatory signaling, and that CNP-miR146a can significantly increase miR-146a gene expression and decrease the downstream expression of proinflammatory cytokines.

Example 6

CNP-miR146a Treatment Reduces Macrophage ROS Production in vitro

Figure 44:
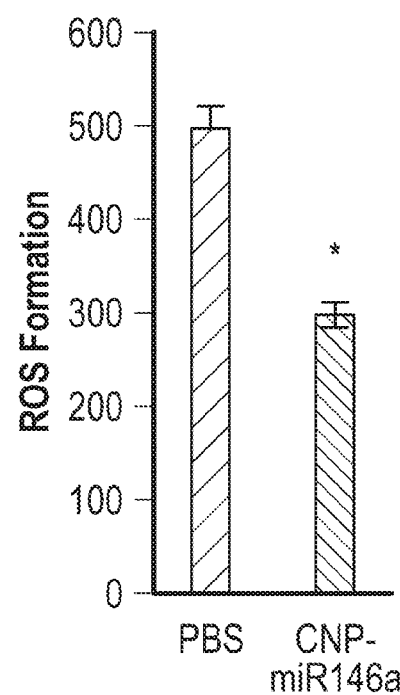
FIG. 44 is a histogram showing macrophage ROS production following CNP-miR146a treatment.

The production of ROS by macrophages following CNP-miR146a treatment was examined. Following overnight serum starvation, macrophages were treated for 24 hours with either PBS or 1 μg CNP-miR146a. Intracellular production of hydroxyl, peroxyl, and other ROS was measured by the Cellular Reactive Oxygen Species Detection Assay Kit (Abcam, USA). In brief, after 24 hrs of incubation with either PBS or 1 μg CNP-miR146a, macrophages were exposed to 2', 7'-dichlorofluorescein diacetate (DCFDA) for 20 min. The level of intracellular ROS was assessed by the fluorescence emitted by DCFDA after conversion to 2', 7'-dichlorofluorescein by the reaction with ROS. The excitation and emission wavelengths were 492 and 521 nm, respectively. ROS levels were recorded as arbitrary units. Treatment with CNP-miR146a resulted in a significant reduction in macrophage ROS production (FIG. 44, *p,0.01). This preliminary in vitro data demonstrates that CNP-miR146a treatment reduces macrophage ROS production in vitro.

Example 7

CNP-miR146a Treatment Promotes Expression of M2c-Associated Genes

Figures 45A, 45B, 45C:
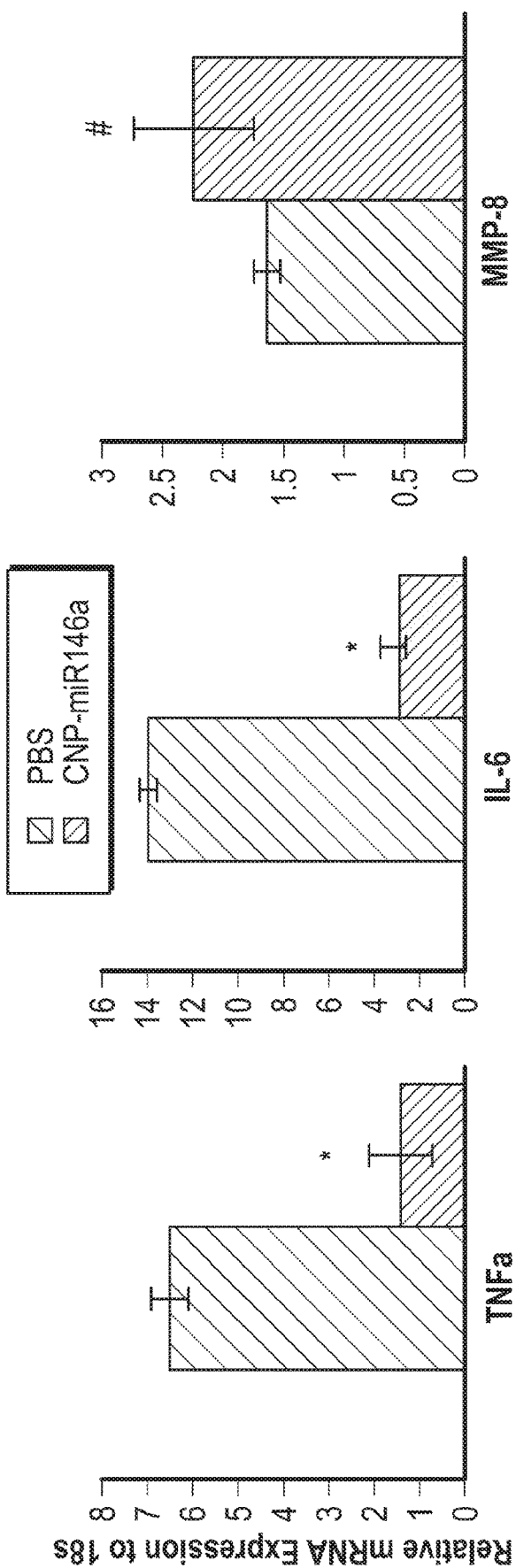
FIGS. 45A-45C are histograms showing macrophage expression of proinflammatory (M1) genes (TNF-a and IL-6) and the regenerative (M2c) gene (MMP8) at baseline and following CNP-miR146a treatment.

The effect of CNP-miR146a conjugates on in vitro macrophage polarization was examined. Macrophages were serum starved overnight in 1% FBS/DMEM and incubated for 24 hours with either PBS or 1 μg of CNP-miR146a. Gene expression of the M1-associated genes, TNF-a and IL-6, as well as the M2c-associated gene, matrix metalloproteinase-8 (MMP-8), was assessed using qPCR. Treatment with CNP-miR146a was associated with significantly decreased gene expression of the M1-associated genes TNF-a and IL-6 (FIGS. 45A-45B, *p<0.01), and significantly increased gene expression of the M2c-associated MMP-8 gene (FIG. 45C, #p<0.05), which has been shown to promote M2-macrophage differentiation and polarization (see, e.g., Wen, et al., J Biol. Chem. 290:19158-19172 (2015)). Accordingly, these results strongly suggest that the CNP-miR146a conjugates of the present technology play a role in M2-type macrophage polarization, switching M1 macrophages to M2 phenotype, and increasing a subject's M2 macrophage pool relative to an untreated control.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for treating or preventing inflammation in a human subject in need thereof, the method comprising:
    administering to the subject a therapeutically effective amount of a pharmaceutical composition comprising microRNA-conjugated cerium oxide nanoparticles (CNPs),
    wherein the microRNA is miRNA 146a covalently attached at a 3' end to the cerium oxide nanoparticle via an amide linkage, and wherein the inflammation is associated with a wound.

2. The method of claim 1, wherein the treating or preventing inflammation results in an increased rate of wound closure in the subject compared to the rate of wound closure in an untreated subject.

3. The method of claim 2, wherein the pharmaceutical composition is topically administered to the wound.

4. The method of claim 2, wherein the pharmaceutical composition is administered daily to the wound.

5. The method of claim 1, wherein the subject is a diabetic subject.

6. The method of claim 1, wherein the surface of the CNPs is coated with one or more biocompatible molecules selected from hyaluronic acid, collagen, and fibrinogen.

7. The method of claim 1, wherein the CNPs have a size range of about 3-5 nm.

8. The method of claim 1, wherein the CNPs are doped with a lanthanide selected from one or more of Europium (Eu), Lanthanum (La), Praseodymium (Pr), Neodymium (Nd), Promethium (Pm), Samarium (Sm), Gadolinium (Gd), Terbium (Tb), Dysprosium (Dy), Homium (Ho), Erbium (Er), Thulium (Tm), Ytterbium (Yb), and Lutetium (Lu).

9. The method of claim 1, wherein the administering is performed topically, intradermally, or intramuscularly.

10. The method of claim 1, wherein the amide linkage between the miRNA 146a and the CNP has the structure:

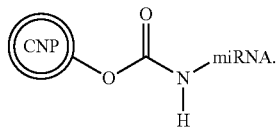

11. A pharmaceutical composition comprising:
miRNA146a; and
cerium oxide nanoparticles (CNPs),
wherein the miRNA146a is covalently attached to the cerium oxide nanoparticles (CNPs) via amide bond at a 3' end of the miRNA 146a, and the conjugated nanoparticles are configured to synergistically reduce oxidative stress and inflammation associated with a wound on a human subject.

12. The pharmaceutical composition of claim 11, wherein the surface of the CNPs is coated with one or more biocompatible molecules selected from hyaluronic acid, collagen, and fibrinogen.

13. The pharmaceutical composition of claim 11, wherein the CNPs have a size range of about 3-5 nm.

14. The pharmaceutical composition of 39, wherein the CNPs are doped with a lanthanide selected from one or more of Europium (Eu), Lanthanum (La), Praseodymium (Pr), Neodymium (Nd), Promethium (Pm), Samarium (Sm), Gadolinium (Gd), Terbium (Tb), Dysprosium (Dy), Homium (Ho), Erbium (Er), Thulium (Tm), Ytterbium (Yb), and Lutetium (Lu).

15. The pharmaceutical composition of claim 11, wherein the amide bond between the miRNA 146a and the CNP has the structure:

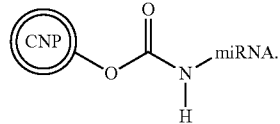

* * * * *